US005554798A

United States Patent [19]

Lundquist et al.

[11] Patent Number: 5,554,798
[45] Date of Patent: Sep. 10, 1996

[54] FERTILE GLYPHOSATE-RESISTANT TRANSGENIC CORN PLANTS

[75] Inventors: Ronald C. Lundquist, Minnetonka; David A. Walters, Bloomington, both of Minn.

[73] Assignee: DeKalb Genetics Corporation, St. Paul, Minn.

[21] Appl. No.: 441,073

[22] Filed: May 15, 1995

Related U.S. Application Data

[63] Continuation of Ser. No. 508,045, Apr. 11, 1990, Pat. No. 5,484,956, which is a continuation-in-part of Ser. No. 467,983, Jan. 22, 1990, abandoned.

[51] Int. Cl.⁶ .............................. A01H 4/00; C12N 15/05
[52] U.S. Cl. .................... 800/205; 800/DIG. 56; 435/172.3; 435/172.1; 435/240.5; 435/240.45; 536/23.71
[58] Field of Search ....................... 800/205, 250, 800/DIG. 56; 435/172.3, 172.1

[56] References Cited

U.S. PATENT DOCUMENTS

| | | | |
|---|---|---|---|
| 4,370,160 | 1/1983 | Ziemelis | 71/117 |
| 4,399,216 | 8/1983 | Axel et al. | 435/6 |
| 4,535,060 | 8/1985 | Comai | 435/172.3 |
| 4,559,301 | 12/1985 | Turner | 435/76 |
| 4,559,302 | 12/1985 | Ingolia | 435/172.3 |
| 4,581,847 | 4/1986 | Hibberd et al. | 47/58 |
| 4,634,665 | 1/1987 | Axel et al. | 435/68 |
| 4,642,411 | 2/1987 | Hibberd et al. | 800/1 |
| 4,665,030 | 5/1987 | Close | 435/240 |
| 4,666,844 | 5/1987 | Cheng | 435/240 |
| 4,683,202 | 7/1987 | Mullis | 435/91 |
| 4,727,028 | 2/1988 | Santerre et al. | 435/240.2 |
| 4,743,548 | 5/1988 | Crossway et al. | 435/172.3 |
| 4,761,373 | 8/1988 | Anderson et al. | 435/172.3 |
| 4,806,483 | 2/1989 | Wang | 435/240.49 |
| 4,940,835 | 7/1990 | Shah et al. | 800/205 |
| 4,971,908 | 11/1990 | Kishore et al. | 435/172.1 |
| 5,001,060 | 3/1991 | Peacock et al. | 435/172.3 |
| 5,004,863 | 4/1991 | Umbeck | 800/205 |
| 5,015,580 | 5/1991 | Christou et al. | 435/172.3 |
| 5,034,322 | 7/1991 | Rogers et al. | 435/172.3 |
| 5,049,500 | 9/1991 | Arnizen et al. | 435/172.3 |
| 5,094,945 | 3/1992 | Comai | 435/172.3 |
| 5,110,732 | 5/1992 | Benfey et al. | 435/172.3 |
| 5,134,074 | 7/1992 | Gordon et al. | 435/240.4 |
| 5,177,010 | 1/1993 | Goldman et al. | 435/172.3 |
| 5,187,073 | 2/1993 | Goldman et al. | 435/172.3 |
| 5,188,642 | 2/1993 | Shah et al. | 47/58 |
| 5,188,958 | 2/1993 | Moloney et al. | 435/240.4 |
| 5,250,515 | 10/1993 | Fuchs et al. | 514/12 |
| 5,254,799 | 10/1993 | DeGrave et al. | 800/205 |
| 5,258,300 | 11/1993 | Glassman et al. | 435/240.4 |
| 5,268,463 | 12/1993 | Jefferson | 536/23.7 |
| 5,290,924 | 3/1994 | Last et al. | 536/24.1 |
| 5,302,523 | 4/1994 | Coffee et al. | 435/172.1 |
| 5,350,689 | 9/1994 | Shillito et al. | 435/240.47 |
| 5,352,605 | 11/1994 | Fraley et al. | 435/240.4 |
| 5,371,003 | 12/1993 | Murray et al. | 435/172.3 |
| 5,405,765 | 4/1995 | Vasil et al. | 435/172.3 |

FOREIGN PATENT DOCUMENTS

| | | | |
|---|---|---|---|
| 80893/87 | 12/1988 | Australia | C12N 15/00 |
| 0126537A2 | 4/1983 | European Pat. Off. | A61K 9/52 |
| 0131623B1 | 1/1984 | European Pat. Off. | C12N 15/11 |
| 0141373A3 | 5/1985 | European Pat. Off. | A01G 7/00 |
| 0154204A2 | 9/1985 | European Pat. Off. | C12N 15/00 |
| 0160390A2 | 11/1985 | European Pat. Off. | A01H 15/10 |
| 0193259A1 | 9/1986 | European Pat. Off. | C12N 15/00 |
| 0204549A2 | 10/1986 | European Pat. Off. | C12N 15/00 |
| 0202668A2 | 11/1986 | European Pat. Off. | C12N 5/02 |
| 0242236A1 | 10/1987 | European Pat. Off. | C12N 15/00 |
| 0242246A1 | 11/1987 | European Pat. Off. | C12N 15/00 |
| 0299552A1 | 1/1988 | European Pat. Off. | C12N 15/00 |
| 0257472A2 | 3/1988 | European Pat. Off. | C12N 15/00 |
| 0262971A2 | 5/1988 | European Pat. Off. | A01H 1/02 |
| 0271408 | 6/1988 | European Pat. Off. | C12N 15/00 |
| 0270356A2 | 6/1988 | European Pat. Off. | C12N 15/00 |
| 0275069A2 | 7/1988 | European Pat. Off. | C12N 15/00 |
| 0280400A2 | 8/1988 | European Pat. Off. | A01C 1/06 |
| 0282164A2 | 9/1988 | European Pat. Off. | C12N 5/00 |
| 0292435A1 | 11/1988 | European Pat. Off. | C12N 15/00 |
| 0289479A2 | 11/1988 | European Pat. Off. | C12N 15/00 |
| 0290395A2 | 11/1988 | European Pat. Off. | C12N 15/00 |
| 0301749A2 | 2/1989 | European Pat. Off. | C12N 15/00 |
| 0353908A2 | 7/1989 | European Pat. Off. | C12N 15/29 |
| 0334539A2 | 9/1989 | European Pat. Off. | C12N 15/00 |
| 0331855A2 | 9/1989 | European Pat. Off. | C12M 3/00 |
| 0348348A2 | 12/1989 | European Pat. Off. | A01N 65/00 |
| 0385962A1 | 2/1990 | European Pat. Off. | C12N 15/82 |
| 0360750A2 | 3/1990 | European Pat. Off. | C12N 15/29 |
| 0359617A2 | 3/1990 | European Pat. Off. | C12N 15/53 |
| 0408403A1 | 5/1990 | European Pat. Off. | C12N 15/32 |
| 0442174A1 | 4/1991 | European Pat. Off. | C12N 15/82 |
| 0424047A1 | 4/1991 | European Pat. Off. | C12N 15/87 |
| 0459643A2 | 5/1991 | European Pat. Off. | C12N 15/82 |
| 0442175A1 | 8/1991 | European Pat. Off. | A01H 1/02 |
| 0452269A2 | 11/1991 | European Pat. Off. | C12N 15/82 |
| 0469273A1 | 2/1992 | European Pat. Off. | C12N 15/82 |
| 0485970A3 | 5/1992 | European Pat. Off. | C12N 15/82 |

(List continued on next page.)

OTHER PUBLICATIONS

"Dekalb Researchers Produce Fertile Corn Plants with Foreign Genes," *ARI Newsletter* (Oct./Nov. 1990).
"Genetic Engineering Advance Announced for Corn Plants," *Investor's Daily*, (Apr. 19, 1990).
"Genetically Engineered Corn: Breakthrough Brings Market Closer," *Genetic Technology News*, 8–11 (Oct. 1990).
"Keystone Crops," *Agricultural Genetics Report*, (Mar./Apr. 1990).

(List continued on next page.)

*Primary Examiner*—Gary Benzion
*Attorney, Agent, or Firm*—Schwegman, Lundberg, Woessner & Kluth, P.A.

[57] ABSTRACT

Fertile transgenic *Zea mays* (corn) plants which stably express heterologous DNA which is heritable are provided along with a process for producing said plants. The preferred process comprises the microprojectile bombardment of friable embryogenic callus from the plant to be transformed. The process may be applicable to other graminaceous cereal plants which have not proven stably transformable by other techniques.

6 Claims, 6 Drawing Sheets

FOREIGN PATENT DOCUMENTS

| | | | |
|---|---|---|---|
| 0589110A1 | 3/1994 | European Pat. Off. | A01N 63/02 |
| 2661421 | 11/1991 | France | C12N 15/09 |
| 0018970 | 9/1882 | Germany . | |
| 3738874A1 | 11/1988 | Germany | A01H 1/06 |
| 4013099A1 | 10/1991 | Germany | C12N 15/82 |
| 61-134343 | 5/1984 | Japan . | |
| 8801444 | 1/1990 | Netherlands | C12N 15/87 |
| 2159173 | 11/1985 | United Kingdom | C12N 15/00 |
| WO85/01856 | 5/1985 | WIPO | A01B 76/00 |
| WO85/02973 | 7/1985 | WIPO | A01J 7/00 |
| WO85/02972 | 7/1985 | WIPO | A01C 1/06 |
| WO87/04181 | 7/1987 | WIPO | C12N 1/00 |
| WO87/05629 | 9/1987 | WIPO | C12N 15/00 |
| WO89/04371 | 5/1989 | WIPO | C12N 21/00 |
| WO89/12102 | 12/1989 | WIPO | C12N 15/00 |
| WO89/11789 | 12/1989 | WIPO | A01H 1/00 |
| WO90/01869 | 3/1990 | WIPO | A01H 1/00 |
| WO90/02801 | 3/1990 | WIPO | C12N 15/32 |
| WO90/10691 | 8/1990 | WIPO | C12N 5/00 |
| WO90/10725 | 9/1990 | WIPO | C23C 16/00 |
| WO91/02071 | 2/1991 | WIPO | C12N 15/82 |
| WO91/04323 | 4/1991 | WIPO | C12N 9/10 |
| WO91/00183 | 5/1991 | WIPO . | |
| WO91/10725 | 7/1991 | WIPO | C12N 5/00 |
| WO91/16432 | 10/1991 | WIPO | C12N 15/31 |
| WO92/06205 | 4/1992 | WIPO | C12N 15/82 |
| WO92/09696 | 6/1992 | WIPO | C12N 15/82 |
| WO92/12250 | 7/1992 | WIPO | C12N 15/82 |
| WO92/19731 | 11/1992 | WIPO | C12N 15/00 |
| WO93/07278 | 4/1993 | WIPO | C12N 15/82 |
| WO93/08682 | 5/1993 | WIPO | A01H 1/00 |
| WO93/14210 | 7/1993 | WIPO | C12N 15/82 |
| WO93/19190 | 9/1993 | WIPO | C12N 15/82 |
| WO93/21335 | 10/1993 | WIPO | C12N 15/87 |

OTHER PUBLICATIONS

Chan, M.-T., et al., "Agrobacterium–Mediated Production of Transgenic Rice Plants Expressing a Chimeric α–Amylase Promoter/β–Glucuronidase Gene," Plant Mol. Biol., 22, 491–506 (1993).

Hiei, Y., et al., "Efficient Transformation of Rice (*Oryza sativa* L.) Mediated by Agrobacterium and Sequence Analysis of the Boundaries of the T–DNA," The Plant J., 6, 271–282 (1994).

Abstract, 35th Annual Maize Genetics Conference, *In Vitro Cellular and Devel. Biol.*, 28:(3) (1992).

"Bullets Transform Plant Cells," *Agricell Report*, 9, 5, (Jul. 1987).

"BioTechnica Applies for Field Test of Genetically Engineered Corn," *Genetic Technology News*, 10(3), (Mar. 1990).

Catalog, *Handbook of Fine Chemicals*, Aldrich Chem. Co., p. 508 (1988).

"Chipping Away at Old Weed Enemies," Farm Science Outlook, *Prairie Farmer* 162, 34 (Feb. 20 1990).

"Corn Transformers Multiply," *Bio/Technol.*, 8, 490 (Jun. 1990).

"Cornell U. Gene Gun Hits Biotech Bullseye," *Agriculture Technology*, p. 13.

"Dalapon," Merck Index, 11th edition, S. Budavae, (ed.), Merck and Co., pp. 405–406 (1989).

Dialog Search of Japanese Patent No. 61–134343 (1986).

EPO Notice Regarding Publication of Bibliographic Data for EPO 0485506 (1992).

"Genes Guns Succeed in Altering Corn," *Biotechnology News*, p. 2 (Apr. 1990).

"Herbicide–Resistant Corn" *CT Academy of Science and Engineering, Case Reports*, 5(4), 6 (1990).

International Search Report, PCT/US 90/04462, mailed Jan. 15, 1991.

International Search Report, PCT/US 90/09699, mailed Aug. 16, 1995.

International Society for Plant Molecular Biology, Program and Abstract, Molecular Biology of Plant Growth and Development, Tuson, Arizona, Oct. 6–11 (1991).

Patent Family Record for Australian Patent 87 80 893.

"Plant Science Research, Inc. Achieves Successful Transformation of Corn," *Genetic Engineering News*, 10(3), 3 (March 1990).

"Shotgunning DNA into Cells," *Genetic Engineering News*, (Jul./Aug. 1987).

"Sticky Ends," *Genetic Engineering News*, 10(5), 1 (May 1990).

"Teams from USDA/Monsanto and DeKalb Genetically Engineer Corn," *Genetic Technology News*, 10(5) (May 1990).

"Two Teams Succeed in Putting Foreign Genes in Corn Plants," *Genetic Engineering Letter*, 10(8), 3 (Apr. 24, 1990).

"USDA Approves More Field Tests," *Genetic Technology News*, 11(7), 12 (Jul. 1991).

"USDA Approves Field Test for BioTechnica's Genetically Engineered Corn," *Genetic Technology News*, 10(7), 6 (Jul. 1990).

Adang, M. J., et al., "Characterized Full–Length and Truncated Plasmid Clones of the Crystal Protein of *Bacillus thuringiensis* subsp. kurstaki HD–73 and Their Toxicity to *Manduca sexta*," Gene, 36, 289–300 (1985).

Ahokas, H. "Transfection of Germinating Barley Seed Electrophoretically with Exogenous DNA," *Theor. Appl. Genet.*, 77, 469–472 (1989).

Ahokes, H. "Electrophoretic transfection of cereal grains with exogenous nucleic acid," Soc. Biochem. Biophys. Microbio. Fen., Biotieteen Paivat (Bioscience Days), Abstracts, Technical University of Helsinki, Espoo, p. 2 (1989).

Akella, V., et al., "Expression in Cowpea Seedings of Chimeric Transgene after Electoporation into Seed–Derived Embryos," *Plant Cell Rep.*, 12, 110–117 (1993).

Altenbach, S. B., et al., "Enhancement of the Methionine Content of Seed Proteins by the Expression of a Chimeric Gene Encoding a Methionine–Rich Protein in Transgenic Plants," *Plant. Mol. Biol.*, 13, 513–522 (1989).

Altenbach, S. B., et al., "Cloning and Sequence Analysis of a cDNA Encoding a Brazil Nut Protein Exceptionally Rich in Methionine," *Plant Mol. Biol.*, 8, 239–250 (1987).

Ampe, C., et al., "The Amino–Acid Sequence of the 2S Sulphur–Rich from Seed of Brazil Nut (*Bertholletia excelsa* H.B.K.)," *Eur. J. Biochem.*, 159, 597–604 (1986).

Armstrong, C. L., et al., "Establishment and Maintenance of Friable, Embryogenic Maize Callus and the Involvement of L–Proline," *Planta*, 164, 207–214 (1985).

Armstrong, C. L., et al., "Genetic and cytogenetic variation in plants regenerated from organogenic and friable, embryonic tissue cultures of maize," *Biological Abstracts*, vol. 85, Abstract No. 117662 (1988).

Aves, K., et al., "Transformation of an Elite Maize Inbred Through Microprojectile Bombardment of Regenerable Embryonic Callus", *In Vitro Cell. Develop. Biol.*, 28A, p. 124A, Abstract No. P–1134 (1992).

Bao-Jian, L., et al., "Introduction of Foreign Genes into the Seed Embryo Cells of Rice by Electroinjection and the Regeneration of Transgenic Rice Plants," *Science in China*, 34, 925–931 (1991).

Barker, R. F., et al., "Nucleotide Sequence of the T–DNA Region from the *Agrobacterium tumefaciens* Octopone Ti Plasmid pTi15955," *Plant Mol. Biol.*, 2, 335–350 (1983).

Beerman, F., et al., "Tyrosinase as a Marker for Transgenic Mice," *Nuc. Acids. Res.*, 19, 958 (1991).

Belanger, F. C., et al., "Molecular Basis for Allelic Polymorphism of the Maize Globulin-1 Gene" *Genetics*, 129, 863–872 (1991).

Benner, M. S., et al., "Genetic Analysis of Methionine–Rich Storage Protein Accumulation in Maize," *Theor. Appl. Genet.*, 78, 761–767 (1989).

Bevan, M., et al., "A Chimaeric Antibiotic Resistance Gene as a Selectable Marker for Plant Cell Transformation," *Nature*, 304, 184–187 (1983).

Bevan, M., et al., "Structure and Transcription of the Nopaline Synthase Gene Region of T–DNA," *Nuc. Acids Res.*, 11, 369–385 (1983).

Binns, A. N., "Agrobacterium–mediated gene delivery and the biology of host range limitations," *Physiologia Plantarium*, 79, 135–139 (1990).

Bishop, J. E., "Two Teams Plane Genes into Corn," *The Wall Street Journal*, B1 (Apr. 1990).

Booy, G., et al., "Attempted Pollen—Mediated Transformation of Maize," *J. Plant Physiol.*, 135, 319–324 (1989).

Boulton, M. I., et al., "Specificity of *Agrobacterium*—mediated delivery of maize streak virus DNA to members of the Gramineae," *Plant Molecular Biology*, 12, 31–40 (1989).

Brill, W. J., "Agricultural Microbiology," *Scientific American*, 245(3), 199–215 (Sep. 1981).

Brunke, K. J., et al., "Insect Control with Genetically Engineered Crops," *Trends in Biotechnol.*, 9, 197–200 (1991).

Buchanan–Wollaston, V., et al., "Detoxification of the Herbicide Dalapon by Transformed Plants," *J. of Cell. Biochem.*, 13D, p. 330, Abstract No. M503 (1989).

Callis, J., et al., "Introns Increase Gene Expression in Cultures Maize Cells," *Genes and Development*, 1, 1183–1200 (1987).

Cao, J., et al., "Transformation of Rice and Maize Using the Biolistic Process," In: *Plant Gene Transfer*, Alan R. Liss, Inc., pp. 21–33 (1990).

Carpita, N. C., "The Biochemistry of "Growing" Cell Walls," In: *Physiology of Cell Expansion During Plant Growth*, Cosgrove, D. J., et al., (eds.) Am. Soc. Plant Physiol., pp. 28–100 (1987).

Chandler, V. L., et al., "Two Regulatory Genes of the Maize Anthocyanin Pathway are Homologous: Isolation of B Utilizing R Genomic Sequences," *The Plant Cell*, 1, 1175–1183 (1989).

Chasan, R., "Transforming Maize Transformation," *The Plant Cell*, 4, 1463–1464 (1992).

Chourey, P. S., et al., "Callus Formation from Protoplasts of a Maize Cell Culture," *Theor. Appl. Genet.*, 59, 341–344 (1981).

Christou, P., et al., "Opine Synthesis in Wild—Type Plant Tissue," *Plant Physiol.*, 82, 218–221 (1986).

Christou, P., et al., "Soybean Genetic Engneering—Commercial Production of Transgenic Plants," *Trends Biotechnol.*, 8, 145–151 (1990).

Christou, P., et al., "Cotransformation Frequencies of Foreign Genes in Soybean Cell Cultures," *Theor. Appl. Genet.*, 79, 337–341 (1990).

Christou, P., et al., "Genetic Transformation of Crop Plants Using Microprojectile Bombardment," *The Plant Journal*, 2, 275–281 (1992).

Christou, P., et al., "Stable Transformation of Soybean Callus by DNA—Coated Gold Particles," *Plant Physiol.*, 87, 671–674 (1988).

Chu, C.—C., et al., Establishment of an Efficient Medium for Anther Culture of Rice Through Comparative Experiments on the Nitrogen Sources," *Sci. Sin. (Peking)*, 13, 659–668 (1975).

Clark, B., "Biotech Advance in Corn: Gunslinging Researchers Fire Marker Genes in to Corn," *AG Consultant*, 46(7), 12(Jul. 1990).

Cocking, F., et al., "Gene Transfer in Cereals," *Science*, 236, 1259–1262 (1987).

Coe et al., "The Genetics of Corn" In: *Corn and Corn Improvement*, 2nd edition, Sprague, G. F., (ed.), American Soc. Agronomy, Inc, Madison, WI, p. 138 (1977).

Comai, L., et al., "Expression in Plants of a Mutant aroA Gene from *Salmonella typhimurium* Confers Tolerance to Glyphosate," *Nature*, 317, 741–744 (Oct., 1985).

Creissen, G., et al., "Agrobacterium— and Microprojectile—Mediated Viral DNA Delivery into Barley Microspore Derived–Cultures," *Plant Cell Rep.*, 8, 680–683 (Apr. 1990).

Crossway, A., et al., "Integration of foreign DNA following microinjection of tobacco mesophyll protoplasts," *Mol. Gen. Genet.*, 202, 179–185 (1986).

D'Halluin, K., et al., "Transgenic Maize Plants by Tissue Electroporation," *The Plant Cell*, 4, 1495–1505 (1992).

Darvill, A., et al., "The Primary Cell Walls of Flowering Plants," In: *The Biochemistry of Plants*, vol. 1, pp. 91–162 (1980).

Dauce–LeReverand, B., et al., "Improvement of *Escherichia coli* Strains Overproducing Lysine Using Recombinant DNA Techniques," *Eur. J. Appl. Microbiol. Biotechnol.*, 15, 227–231 (1982).

De Block, M., et al., "Engineering herbicide resistance on plants by expression of a detoxifying enzyme," *EMBO J.*, 6, 2513–2518 (1987).

De Greef, W., et al., "Evaluation of herbicide resistance in transgenic crops under field conditions," *Bio/Technol.*, 7, 61–64 (1989).

Dekeyser, R. A., et al., "Evaluation of Selectable Markers for Rice Transformation," *Plant Physiol.*, 90, 217–223 (1989).

Dekeyser, R. A., et al., "Transient Gene Expression in Intact and Organized Rice Tissues," *The Plant Cell*, 2, 591–602, (1990).

DeWald et al., "Plant regeneration from inbred maize suspensions," VIIth International Congress on Plant Tissue and Cell Culture, p. 12, Abstract No. A1–36 (Jun. 24–29, 1990).

DeWet, J. M. J., et al.; "Exogenous gene transfer in maize (*Zea mays*) using DNA–treated pollen;" In: *The experimental manipulation of ovule tissues*. Chapman, G. P., et al., (eds.), Longman, New York, pp. 197–209 (1985).

DeWet, J. R. et al., "Cloning of Firefly Luciferase cDNA and the Expression of Active Luciferase in *Escherichia coli*," *Proc. Nat. Acad. Sci. USA*, 82, 7870–7873 (1985).

Donn, G., et al., "Stable Transformation of Maize with a Chimaeric, Modified Phosphinothricin–Acetyltransferase Gene from *Streptomyces viridochromogenes*," Abstracts, VIIth International Congress Plant Tissue Cell Culture, p. 53, Abstract No. A2-38 (Jun. 24–29, 1990).

Dupuis, I., et al., "Gene Transfer to Maize Male Reproductive Structure by Particle Bombardment of Tassel Primordia," *Plant Cell Rep.*, 12, 607 (1993).

Ellis, J. G., et al., "Does the OCS–Element Occur as a Functional Component of the Promotors of Plant Genes?" *EMBO J.*, 6, 3203–3208 (1987).

Evans, D. A., et al., "Somaclonal Variation—Genetic Basic and Breeding Applications," *Trends Genet.*, 5, 46–50 (1989).

Fennel, A., et al., "Electroporation and PEG Delivery of DNA into Maize Microspores," *Plant Cell Reports*, 11, 567–570 (1992).

Fitzpatrick, T., "Pleiotrophic Gene Found in Barley Plant," *Genetic Engineering News*, 13, 1 (1993).

Fransz, P., et al., "Cytodifferentiation during callus initiation and somatic embryogenesis in *Zea mays* L.," Ph.D. thesis, U. of Wageningen Press, The Netherlands (1988).

Freeling, J. C., et al., "Developmental Potentials of Maize Tissue Cultures," *Maydica*, XXI, 97–112 (Jul. 1977).

Freiberg, "More Researchers Discover Corn Transformation Technology," *AG Biotechnology News*, p. 26 (1990).

Fromm, M. E., et al., "Inheritance and Expression of Chimeric Genes in the Progeny of Transgenic Maize Plants," *Bio/Technol.*, 8, 833–839 (1990).

Fromm, M. E., et al., "Stable Transformation of Maize after Gene Transfer by Electroporation," *Nature*, 319, 791–793 (1986).

Fromm, M., et al., "Expression of Genes Transfected into Monocot and Dicot Plant Cells by Electroporation," *Proc. Nat. Acad. Sci. USA*, 82, 5824–5828 (1985).

Fry, S. C., "Introduction to the Growing Cell Wall," In: *The Growing Plant Cell Wall: Chemical and Metabolic Analysis*, Longman Scientific and Technical, New York, pp. 1–5, 102–109 (1988).

Geiser, M., et al., "The Hypervariable Region on the Genes Coding for Entomopathogenic Crystal Proteins of *Bacillus thuringiensis*: Nucleotide Sequence of the *kurhd1* gene of subsp. *kurstaki* HD1," *Gene*, 48, 109–118 (1986).

Goff, S. A., et al., "Plant Regeneration of Anthocyanin Biosynthetic Genes Following Transfer of B Regulatory Genes into Maize Tissues," *EMBO J.*, 9, 2517–2522 (1990).

Gordon–Kamm, W. J., et al., "Stable Transformation of Embryonic Maize Cultures by Microprojectile Bombardment," *J. Cellular Biochem.*, 13D, p. 259, Abstract No. M122 (1989).

Gordon–Kamm, W. J., et al., "Transformation of Maize Cells and Regeneration of Fertile Transgenic Plants," *The Plant Cell*, 2, 603–618 (1990).

Gould, J., et al., "Transformation of the Graminae by *Agrobacterium tumefaciens*," Int. Soc. Plant Mol. Biol. 3rd Int. Congress, Abstract No. 1277 (1991).

Gould, O., et al., "Shoot Tip Culture as a Potential Transformation System," Abstracts, Beltwide cotton production research conferences, New Orleans, LA, p. 91 (1988).

Gould, J., et al., "Transformation of *Zea mays* L. Using *Agrobacterium tumefaciens* and the Shoot Apex," *Plant Physiol.* 95, 426–434 (1991).

Graves, A., et al., "The Transformation of *Zea mays* seedings with *Agrobacterium tumefacians*," *Plant Mol. Biol.*, 7, 43–50 (1986).

Green, C., et al., "Plant Regeneration from Tissue Cultures of Maize," *Crop. Sci.*, 15, 417–421 (1975).

Green, C., et al., "Plant Regeneration in Tissue Cultures of Maize," In: *Maize for Biological Research*, Sheridan, W. F., (ed.) Plant Mol. Biol. Assoc., pp. 367–372 (1982).

Green, C., et al., "Somatic Cell Genetic Systems, in Corn," In: *Advances in Gene Technology: Molecular Genetics of Plant and Animals*, Academic Press, Inc., pp. 147–157 (1983).

Grimsley, N., et al., "DNA Transfer from Agrobacterium to *Zea mays* or *Brassica* by Agroinfection is Dependent on Bacterial Virulence Functions," *Mol. Gen. Genet.*, 217, 309–316 (1989).

Gritz, L., et al., "Plasmid—Encoded Hygromycin B Resistance: The Sequence of Hygromycin B Phosphotransferase Gene and Its Expression in *Escherichia coli* and *Saccharomyces cerevisiae*," *Gene*, 25, 179–188 (1983).

Guerineau, F., et al., "Sulfonamide Resistance Gene for Plant Transformation," *Plant Molecular Biology*, 15, 127–136 (1990).

Guilley, H., et al., "Transcription of Cauliflower Mosaic Virus DNA: Detection of Promoter Sequences, and Characterization of Transcripts," *Cell*, 30, 763–773 (Oct. 1982).

Gunset, G., "Genetic Advance May Transform Corn," *Chicago Tribune* (Apr. 19, 1990).

Gunset, G., "Corn Farmers See Economic, Environmental Gold in Designer Genes," *Chicago, Tribune* (Jan. 21, 1991).

Hallauer, A. R., et al., "Corn Breeding," In: *Corn and Corn Improvement*, 3rd edition, Sprague, G. F., et al., (eds.), Agronomy Soc. Amer., pp. 463–564 (1988).

Haughn, G. W., "Transformation with a Mutant Arabidopsis Acetolactate Synthase Gene Renders Tobacco Resistant to Sulfonylurea Herbicides," *Mol. Gen. Genet.*, 211, 266–271 (1988).

Hautpman, R. M., et al., "Evaluation of Selectable Markers for Obtaining Stable Transformants on the Gramineae," *Plant Physiol.*, 86, 602–606 (1988).

Hoffman, L. M., et al., "A Modified Storage Protein is Synthesized, Processed, and Degraded in the Seeds of Transgenic Plants," *Plant Mol. Biol.*, 11, 717–729 (1988).

Hoffman, L. M., et al., "Synthesis and Protein Body Deposition of Maize 15kD Zein in Transgenic Tobacco Seeds," *EMBO J.*, 6, 3213–3221 (1987).

Hofte, H., et al., "Insecticidal Crystal Proteins of *Bacillus thuringiensis*," *Microbiol. Rev.*, 53, 242–255 (1989).

Hong, B., et al., "Developmental and Organ—Specific Expression of an ABA—and Stress–Induced Protein in Barley," *Plant Mol. Biol.*, 18, 663–674 (1992).

Hooykaas, P. J. J., "Transformation of plant cell via Agrobacterium," *Plant Mol. Biol.*, 13, 327–336 (1989).

Horn, M., et al., "Transgenic Plants of Orchard Grsss (*Dactylis glomerata L.*) from Protoplasts," *Chem. Abstracts*, 110, p. 208, Abstract no. 89869a (1989).

Horn, M., et al., "Transgenic Plants of Orchard grass (*Dactylis glomerata L.*) from Protoplasts," *Plant Cell Reports*, 7, 469 (1988).

Howe, A., et al., "Development of Glyphosphate as a Selectable Marker for the production of Fertile Transgenic Corn Plants," *In Vitro Cell Develop. Biol.*, 28A, p. 124A, Abstract No. P-1136 (Jul.–Aug. 1992).

Huang, Y., et al., "Factors Influencing Stable Transformation of Maize Protoplasts by Electroporation," *Plant Cell, Tissue and Organ Culture*, 18, 281 (1989).

Imbrie–Milligan, C., et al., "Microcallus Growth from Maize Protoplasts," *Planta*, 171, 58–64 (1987).

Jahne, A., et al., "Regeneration of Fertile Plants from Protoplasts Derived from Embryogenic Cell Suspensions of Barley (*Hordeum vulgare L.*)," *Plant Cell Rep.*, 10, 1–6 (1991).

Jayne, S., et al., "Anslysis of Elite Transgenic Maize Plants Produced by Microprojectile Bombardment," Program and Abstracts, Int. Soc. for Plant Mol. Biol., 3rd Int. Cong., Abstract No. 338 (Oct. 6–11, 1991).

Jefferson, R., et al., "β–Glucuronidase from *Escherichia coli* as a Gene–Fusion Marker," *Proc. Nat. Acad. Sci. USA*, 83, 8447–8451 (1986).

Jefferson, R., et al., "GUS Fusions: β–Glucuronidase as a Sensitive and Versatile Gene Fusion Marker in Higher Plants," *EMBO J.*, 6, 3901–3907 (1987).

Jefferson, R., "Assaying chimeric genes in plants: the GUS gene fusion system," *Plant Mol. Biol. Rep.*, 5, 387–405 (1987).

Jones, H., et al., "Recent Advances in Plant Electroporation," *Oxford Surveys of Plant Molecular and Cell Biol.*, 4, 347–357 (1987).

Jones, H., et al., "Transient Gene Expression in Electroporated Solanum Protoplasts," *Plant Mol. Biol.*, 13, 503–511 (1989).

Kaeppler, H. F., et al., "Silicon Carbide Fiber–Mediated DNA Delivery into Plant Cells," *Plant Cell Rep.*, 9, 415–418 (1990).

Kamo, K., et al., "Establishment and Characterization of Long–Term Embryonic Maize Callus and Cell Suspension Cultures," *Plant Sci.*, 45, 111–117 (1986).

Kamo, K, et al., "Regeneration of *Zea mays L.* from Embryogenic Callus," *Bot Gaz.*, 146, 327–334 (1985).

Kao, K. N., et al., "Nutritional Requirements for Growth of *Vicia hajastana* Cells and Protoplasts at a Very Low Population Density in Liquid Media," *Planta*, 126, 105–110 (1978).

Kartha, K., et al., "Transient Expression of Chloramphenicol Acetyl Transferase (CAT) Gene in Barley Cell Cultures and Immature Embryos Through Microprojectile Bombardment," *Plant Cell Rep.*, 8, 429–432 (1989).

Kay, R., et al., "Duplication of CaMV 35S Promoter Sequences Creates a Strong Enhancer for Plant Genes," *Science*, 236, 1299–1302 (Jun. 5, 1987).

Kirihara, J., et al., "Differential Expression of a Gene for a Methionine—Rich Storage Protein in Maize," *Mol. Gen. Genet.*, 211, 477–484 (1988).

Kirihara, J., et al., "Isolation and Sequence of a Gene Encoding a Methionine–Rich 10–kD Zein Protein from Maize," *Gene*, 71, 359–370 (1988).

Klein, T., et al., "Transfer of Foreign Genes into Intact Maize Cells with High–Velocity Microprojectiles," *Proc. Nat. Acad. Sci. USA*, 85, 4305–4309 (1988).

Klein, T. M., et al., "Factors Influencing Gene Delivery into *Zea mays* Cells by High Velocity Microprojectiles," *Bio/Tec* 6, 559–563 (1988).

Klein, T. M., et al., "High–Velocity Microprojectiles for Delivering Nucleic Acids to Living Cells," *Nature*, 327, 70–73 (1987).

Klein, T., et al., "Genetic Transformation of Maize Cell by Particle Bombardment and the Influence of Methylation on Foreign Gene Expression," In: *Gene Manipulation in Plant Improvement II*, Gustafson, J. P., (ed.), Plenum Press, NY, pp. 265–266 (1990).

Klein, T., et al., "Genetic Transformation of Maize Cells by Particle Bombardment," *Plant Physiol.*, 91, 440–444 (1989).

Klein, T., et al., "Regulation of Anthocyanin Biosynthetic Genes Introduced into Intact Maize Tissue by Microprojectiles," *Proc. Nat. Acad. Sci. USA*, 86, 6682–6685 (1989).

Kozak, M., "Compilation and Analysis of Sequence from the Translational Start Site in Eukaryotic mRNAs," *Nuc. Acids. Res.*, 12, 857–871 (1984).

Kozak, M., "Point Mutations Define a Sequence Flanking the AUG Initiator Codon that Modulates Translation by Eukaryotic Ribosomes," *Cell*, 44, 283–292 (1986).

Koziel, M. G., et al., "Field Performance of Elite Transgenic Maize Plants Expressing an Insecticidal Protein Derived from *Bacillus thuringenesis*," Bio/Technol., 11, 194–200 (1993).

Kreitlow, B., "Genetic Engineering 'Breakthrough' Disputed," Cedar Rapids Gazette (Apr. 20, 1990).

Kriz, A. L., et al., "Characterization of the Maize Globulin-2 Gene and Analysis of Two Null Alleles," *Biochemical Genetics*, 29, 241–254 (1991).

Kuhlemeier, C., et al., "Regulation of Gene Expression in Higher Plants," *Ann. Rev. Plant Physiol.*, 38, 234–239 (1987).

Langridge, et al., "Transformation of Cereals via Agrobacterium and the Pollen Pathway: A Critical Assessment," *The Plant J.*, 2, 613–638 (1992).

Laursen, C. M., et al., "Production of Fertile Transgenic Maize by Electorporation of Suspension Culture Cells," *Plant Mol. Biol.*, 24, 51–61 (1994).

Lazzeri, P., et al., "In Vitro Genetic Manipulation of Cereals and grasses," *Ad. Cell Culture*, 6, 291–293 (1988).

Lee, J. S., et al., "Gene Transfer into Intact cells of Tobacco by Electroporation," *Korea J. Gent.*, 11, 65–72 (1989).

Leemans, J., "Genetic Engineering for Fertility Control," Keystone Symposium on Crop Improvement via Biotechnology: An International Perspective, Abstract No. Y016 (Apr. 10–26, 1992).

Levitt, J. "Growth Regulators" In: *Introduction to Plant Physiology*, The C. V. Mosby Company, St. Louis, p. 241 (1969).

Li, X.–Q., et al., "GUS Expression in Rice Tissues Using Agrobacterium—Mediated Transformation," Program and Abstracts, Int. Soc. for Plant Mol. Biol., 3rd Int. Cong., Abstract No. 385 (Oct. 6–11, 1991).

Lindsey, K., et al., "Electroporation of Cells," *Physiologia Plantarum*, 79, 168–172 (1990).

Lindsey, K., et al., "The Permeability of Electroporated Cells and Protoplasts of Sugar Beet," *Planta*, 172, 346–355 (1987).

Lindsey, K., et al., "Transient Gene Expression in Electroporated Protoplasts and Intact Cells of Sugar Beet," *Plant Mol. Biol.*, 10, 43–52 (1987).

Lindsey, K. et al., "Stable Transformation of Sugarbeet Protoplasts by Electroporation," *Plant Cell Rep.*, 8, 71–74 (1989).

Looker, D., "Dekalb Claims Success in Effort to Alter Genetic Makeup of Corn," *Des Moines Register* (Apr. 19, 1990).

Lopes, M. A., et al., "Endosperm Origin, Development, and function," *The Plant Cell*, 5, 1383–1399 (1993).

Lorz, H., et al., "Advances in Tissue Culture and Progress Towards Genetic Transformation of Cereals," *Plant Breeding*, 100, 1–25 (1988).

Lu, C., et al., "Somatic Embryogenesis in *Zea mays L.*," *Theor. Appl. Genet.*," 62, 109–112 (1982).

Lu, C., et al., "Improved Efficiency of Somatic Embryogenesis and Plant Regeneration on Tissue Cultures of Maize (Zea mays L.)," Theor. Appl. Genet., 66, 285–289 (1983).

Ludwig, S., et al., "A Regulatory Gene as a Novel Visible Marker for Maize Transformation," Science, 247, 449–450 (1990).

Ludwig, S., et al., "High Frequency Callus Formation from Maize Protoplasts," Theor. Appl. Genet., 71, 344–350 (1985).

Ludwig, S., et al., "Lc, a Member of the Maize R Gene Family Responsible for Tissue–Specific Anthocyanin Production, Encodes a Protein Similar to Transcriptional Activators and Contains the myc–Homology Region," Proc. Nat. Acad. Sci. USA, 86, 7092–7096 (1989).

Ludwig, S., et al., "Maize R Gene Family: Tissue—Specific Helix–Loop–Helix Proteins," Cell, 62, 849–851 (1990).

Lutcke, H., et al., "Selection of AUG Initiation Codones Differs in Plants and Animals," EMBO J., 6, 43–48 (1987).

Maas, C., et al., "A Highly Optimized Monocot Expression Cassette: Application for Barley Transformation and Barley Virus Research," Program and Abstracts, Int. Soc. Plant Mol. Biol., Abstract No. 386 (Oct. 6–11, (1991).

Maddock, S. E., et al., "Expression in Maize Plants of Wheat Germ Agglutinin, a Novel Source of Insect Resistance," Program and Abstracts, Int. Soc. Plant Mol. Biol., 3rd Int. Cong., Abstract no. 372 (Oct. 6–11, 1991).

Masumura, T., et al., "cDNA Cloning of an mRNA Encoding a Sulfur–Rich 10 kDa Prolamin Polypeptide in Rice Seeds," Plant Mol. Biol., 12, 123–130 (1989).

McCabe et al., "Stable Transformation of Soybean (Glycine max) by Particle Acceleration," Bio/Technol, 6, 923–926 (1988).

McDaniel, C., et al., "Cell—Lineage Patterns in the Shoot Apical Meristem of the Germinating Maize Embryo," Planta, 175, 13–22 (1988).

Meadows, M., "Characterization of Cells and Protoplasts of the B73 Maize Cell Line," Plant Sci. Lett., 28 337–348 (1982/83).

Mendel, R., et al., "Delivery of Foreign Genes to Intact Barley Cell by High–Belocity Microprojectiles," Theor. Appl. Genet., 78, 31–34 (1989).

Messing, J., "Corn Storage Protein: A Molecular Genetic Model," Division of Energy BioSciences—Summaries of FY 1990 Activities, p. 70, Abstract No. 135 (1990).

Moffat, A. S., "Corn Transformed," Science, 249, 630 (Aug. 10, 1990).

Morkawa, et al., "Gene Transfer into Intact Plant Cells by Electroporation Through Cell Walls and Membranes," Gene, 41, 121 (1986).

Morocz, S. et al., "An Improved System to Obtain Fertile regenerants via Maize Protoplasts Isolated From a Highly Embryonic Suspension Culture," Theor. Appl. Genet., 80, 721–726 (1990).

Morocz, S., et al., "Two Approaches to Rendering Zea mays L. Applicable to Tissue Culture Manipulations," Abstracts, VIIth Int. Cong. on Plant Tissue and Cell Culture, Amsterdam A1–102, Abstract No. 209, p. 190 (1990).

Murakami, T., et al., "The Bialaphos Biosynthetic Genes of Streptomyces hygroscopicus: Molecular Cloning and Characterization of the Gene Cluster," Mol. Gen. Genet., 205, 42–50 (1986).

Murashige, T., et al., A Revised Medium for Rapid Growth and Bio Assays with Tobacco Tissue Cultures," Physiol. Plant., 15, 473–497 (1962).

Murphy, H. L., "New Dekalb–Pfizer Seed Chief to Harvest R & D Breakthroughs," Crain's Business Weekly, pp. 38–39 (1990).

Murray, E. E., et al., "Codon usage in plant geners," Nuc. Acids Res., 17, 477–498 (1989).

Murry, L. E., et al., "Transgenic Corn Plants Expressing MDMV Strain B Coat Protein are Reistant to Mixed Infections of Maize Dwarf Mosaic Virus and Maize Chlorotic Mottle Virus," Bio/Technol., 11, 1559–1564 (1993).

Nelson, R. S., "Virus Tolerance, Plant Growth, and Field Performance of Transgenic Tomato Plants Expressing Coat Protein from Tobacco Mosaic Virus," et al., Bio/Technol., 6, 403–409 (1988).

Nelson, T., "New Horses for Monocot Gene Jockeys," The Plant Cell, 2, 589 (1990).

Neuffer, "Growing Maize for Genetic Purposes," Maize for Biological Research, Plant Mol. Biol. Assoc., (1988).

Odell, J., et al., "Identification of DNA Sequences Required for Activity of the Cauliflower Mosaic Virus 35S Promoter," Nature, 313, 810–811 (1985).

Office Action dated May 30, 1989, Goldman et al., USSN 06/880,271, filed Jun. 30, 1986.

Office Action dated Mar. 8, 1990, Goldman, USSN 06/880, 271, filed Jun. 30, 1986.

Ohta, Y., "High—Efficiency Genetic Transformation of Maize by a Mixture of pollen and Exogenous DNA," Proc. Nat. Acad. Sci. USA, 83, 715–719 (1986).

Okta, Y., et al., "Gene Manifestation of Exogenuous DNA Applied to Self—Propagating Stigma (Gene Action Revealed in the $M_1$ and $M_2$ Generations from Self–Pollination Applying Exogenous DNA)," Jap. J. Breed., 30 184–185 (1980).

Omirullen, S., et al., "Activity of a Chimeric Promoter with the Doubled CaMV 35S Enhancer in Protoplast–Derived Cells and Transgenic Plants in Maize," Plant Mol. Biol., 21, 415–428 (1993).

Ozias–Akins, P., et al., "In vitro regeneration and genetic manipulation of grasses," Physiol. Plant., 73, 565–569 (1988).

Ozias–Akins, P., et al., "Progress and Limitations in the Culture of Cereal Protoplasts," Trends in Biotechnol, 2, 119–123 (1984).

Park, S. H., et al., "Selection of Maize Transformants from Shoot Apex cultures Cocultivated with Agrobacterium Containing the Bar Gene," In Vitro Cell. Develop. Biol., 29A, p. 85A, Abstract No. P–1102 (1993).

Parker, W. B., et al., "Selection and Characterization of Sethoxydim—Tolerant Maize Tissue Cultures," Plant Physiol., 92, 1220–1225 (1990).

Pederson, K., et al., "Sequence Analysis and Characterization of a Maize Gene Encoding a High–Sulfur Zein Protein of $M_r$ 15,000," J. Biol. Chem., 261, 6279–6284 (1986).

Perl, A., et al., "Bacterial Dihydrodipicolinate Synthase and Desensitized Aspartate Kinase: Two Novel Selectable Markers for Plant Transformation," Bio/Technol., 11, 715–718 (1993).

Perlack, F. J., et al., "Modification of the Coding Sequence Enhances Plant Expression of Insect Control Protein Genes," Proc. Nat. Acad. Sci. USA, 88, 3324–3328 (1991).

Phillips, R. L., et al., "Elevated Protein—Bound Methionine in Seeds of a Maize Line Resistant to Lysine Plus Threonine," Cerial Chem., 62, 213–218 (1985).

Phillips, R. L., et al., "Cell/Tissue Culture and In Vitro Manipulation," In: *Corn and Corn Improvement*, 3rd edition, Sprague, G. F., et al., (eds.), Agronomy Soc. Amer., pp. 345–387 (1988).

Pioneer HiBred International, Inc., *Application Under 7 CFR 340*, Release of Genetically Engineered Corn Plants, Permit No. 92–174–02, NO CBI, p. 8 (Nov. 3, 1992).

Pioneer HiBred International, Inc., *Application Under 7 CFR 340*, Release of Genetically Engineered Corn Plants, Permit No. 92–330–01, CBI–Deleted, p. 13 (Apr. 13, 1993).

Philips, R. L., et al., "Elevated Protein—Bound Methionine in Seeds of a Maize Line Resistant to Lysine plus Threonine," *Cereal Chem.*, 62, 213–218 (1985).

Pioneer's Application for Release in the *Environment Under 7CFR 340*, Corn Plants Genetically Enginerred to Express Wheat Germ Agglutinin (WGA) Genes, in Order to Confer Resistance to the Europeans Corn Borer (*Ostrinia nubilalis*) and Tolerance to Glufosinate Herbicides, 92–022–02, No CBI Copy, p. 11 (May 4, 1992).

Pochlman, J. "Breeding Corn (Maize)," In: *Breeding Field Crops*, 3rd edition, AVI Publishing Co., Westport CN, pp. 452 (1986).

Proehlman, J. Breeding Corn (Maize), "In: *Breeding Field Crops*, 3rd edition, AVI Publishing Co., Westport CN, pp. 469–471, 477–481 (1986).

Potrykus, I., et al., "Callus Formation from Cell Culture Protoplasts of Corn (*Zea mays L.*)," *Theor. Appl. Genet.*, 54, 209–214 (1979).

Potrykus, I., "Gene Transfer to Cereals: An Assessment," *Bio/Technol.*, 8, 535–542 (Jun. 1990).

Potrykus, I., "Gene Transfer to Cereals: An Assessment," *Trends Biotechnol*, 7, 269–273 (Oct. 1989).

Potrykus, I., "Gene Transfer to Plants: Assessment and Perspectives," *Physiol. Plant.*, 79, 125–134 (1990).

Potrykus, I., et al., "Callus formation from stem protoplasts of corn (*Zea mays L.*)" *Mol. Gen. Genet.*, 156, 347–350 (1977).

Potter, et al., "Enhancer—Dependent Expression of Human K Immunoglobulin Genes Introduced into Mouse Pre–B Lymphocytes by Electroporation," *Proc. Nat. Acad. Sci. USA*, 81, 7161 (1984).

Prioli, L. M., et al., "Plant Regeneraton and Recovery of Fertile Plants from Protoplasts of Maize (*Zea mays L.*)," *Bio/Technol.* 7, 589–594 (Jun. 1989).

Puite, K. J., et al., "Electrofusion, a Simple and Reproducible Technique in Somatic Hybridization of *Nicotiana plumbaginifolia* mutants," *Plant Cell Rep.*, 4, 274–276 (1985).

Rasmusen, J. L., et al., "Biolistic Transformation of Tobacco and Maize Suspension Cells Using Bacterial Cells as Microprojectiles," *Plant Cell Rep.* 13, 212–217 (1994).

Rhodes, C. A., et al., "Genetically Transformed Maize Plants from Protoplasts," *Science*, 240, 204–207 (Apr. 8, 1988).

Rhodes, C. A., et al., "Plant Regeneration from Protoplasts Isolated from Embryogenic Maize Cell Cultures," *Bio/Technol.*, 6, 56–60 (Jan. 1988).

Rhodes, C. A., "Corn: From Protoplasts to Fertile Plants," *Bio/Technol.*, 7, 548 (Jun. 1989).

Richaud, F., et al., "Chromosomal Location and Nucleotide Sequence of the *Escherichia coli dapA* Gene," *Biol. Abstracts*, 82, p. AB–391, Abstract No. 3396 (1986).

Richaud, F., et al., "Chromosomal Location and Nucleotide Sequence of the *Escherichia coli dapA* Gene," *J. Bacteriol*, 166, 297–300 (1986).

Robbins-Roth et al., "They Make it Happen in Biotech," *Bioworld*, pp. 30–36 (Nov./Dec. 1990).

Robertson, D. S., "Loss of Mu Mutator Activity when Active Mu Systems are Transferred to Inbred Lines," *Maize Genetics Coop. Newsletter*, 60, 10 (1986).

Ross, M. C., et al., "Transient and Stable Transgenic Cells and Calli of Tobacco and Maize Following Microprojectile Bombardment," *J. Cell. Biochem.*, 13D, p. 268, Abstract No. M149 (1989).

Sahi, S. V., et al., "Metabolites in Maize Which Affect Virulence Induction in *Agrabacterium tumefaciens*," *Plant Physiol, Supplement*, p. 86, Abstract No. 514, (1989).

Sanford, J. C., "Biolistic Plant Transformation," *Physiol. Plant.*, 79, 206–209 (1990).

Sanford, J. C., "The Biolistic Process," *Trends Biotechnol.*, 6, 299–302 (1988).

Sanford, J. C., et al., "Attempted Pollen—Mediated Plant Transformation Employing Genomic Donor DNA," *Theor. Appl. Genet.*, 69, 571–574 (1985).

Sanford, J. C., et al., "Delivery of Substances into Cells and Tissues Using a Particle Bombardment Process," *Particulate Sci. Technol.*, 5, 27–37 (1987).

Sass, "Morphology: Development of the Caryopsis" In: *Corn and Corn Improvement*, 2nd edition, Sprauge, G. F., (ed.), American Soc. Agronomy, p. 89, 98 (1977).

Schmidt, A., et al., "Media and environmental effects of phenolics production from tobacco cell cultures," *chem. Abstracts*, 110, p. 514, Abstract No. 230156z (1989).

Shen, W.–H., et al., "Excision of a Transposible Element form a Viral Vector Introduced into Maize Plants by Agroinfection," *The Plant J.*, 2, 35–42 (1992).

Shen, W.–H., et al., "Amplification and expression of the β–glucuronidase gene in maize plants by vectors based on maize streak virus," *The Plant Journal*, 5, 227–236 (1994).

Shigekawa, K., et al., "Electroporation of Eukaryotes and Prokaryotes: A General Approach to the Introduction of Macromolecules into Cells," *Bio Techniques*, 6, 742–751 (1988).

Shillito, R. D., et al., "High Efficiency Direct Gene Transfer to Plants," *Bio/Technol.*, 3, 1099 (1985).

Shillito, R. D., et al., "Regeneration of Fertile Plants From Protoplasts of Elite Inbred Maize," *Bio/Technol.*, 7, 581–587 (Jun. 1989).

Shimamoto, K., et al., "Fertile Transgenic Rice Plants Regenerated from Transformed Protoplasts," *Nature*, 338, 274–278 (1989).

Shotwell, M. A., et al., "The Biochemistry of Plants—A Comprehensive Treatise," In: *The Biochemistry of Plants*, vol. 15, Marcus, A., (ed.), Academic Press, Inc., San Diego, pp. 297–345 (1989).

Smith, R., et al., "Shoot apex explant for transformation," *Plant Physiol.*, 86, p. 108, Abstract No. 646 (1988).

Soberon, X., et al., "Construction and Characterization of New Cloning Vehicles, IV. Deletion Derivatives of pBR322 and pBR325," *Gene*, 9, 287–305 (1980).

Songstad, D. D., et al., "Transient Expression of GUS and Anthocyanin Constructs in Intact Maize Immature Embryos Following Electroporation," *Plant Cell Tissue and Organ Culture*, 33, 195–201 (1993).

Spencer, T. M. et al., "Fertile Transgenic Maize," Abstracts, 7th Annual Meeting, Mid Atlantic Plant Mol. Biol. Soc. p. 30 (1990).

Spencer et al., "Bialaphos Selection of Stable Transformations from Maize Cell Culture," *Theor. Appl. Genet.*, 79, 625–631 (May 1990).

Spencer, T. M., et al., "Segregation of Transgenes in Maize," *Plant Mol. Biol.*, 18, 201–210 (1992).

Spencer, T. M., et al., "Selection of Stable Transformants from Maize Suspension Cultures using the Herbicide Bialaphos," Poster presentation, FASEB Plant Gene Expression Conference, Copper Mountain, Colorado (Aug. 8, 1989).

Sprauge et al., "Corn Breeding," In: *Corn and Corn Improvement*, Sprauge, G. F., (ed.), American Society of Agronomy, Inc, Madison, Wi, pp. 305, 320–323 (1977).

Steimel, D., "Corn Breeders Stalk Perfect Hybrid," *Rockford Register Star.* (Aug. 6, 1990).

Steimel, D., "New Gun Will Custom–Design Corn: Breeding Technique Expected by End of '90's Will Let Crop Grow Without Pesticides or Much Water," (Apr. 1990).

Sugiyama, M., et al., "Use of the Tyrosinase Gene from Streptomyces to Probe Promoter Sequences for *Escherichia coli,"Plasmid*, 23, 237–241 (1990).

Suttie, J., et al., "Use of Different Selection Agents to Produce Maize Transformants of an Elite Geneotype Using Microprojectile Bombardment," Program and Abstracts, Int. Soc. Plant Mol. Biol., 3rd Int. Cong., Abstract No. 426 (Oct. 6–11, 1991).

Tarczynski, M. C., et al., "Expression of a Bacterial mtlD Gene in Transgenic Tobacco Leads to Production and Accumulation of Mannitol," *Proc. Nat. Acad. Sci. USA*, 89, 2600–2604 (1992).

Tarczynski, m. C., et al., "Stress Protection of Transgenic Tobacco by Production of the Osmolyte Mannitol," *Science*, 259, 508–510 (1993).

Thompson, C., et al., "Characterization of the Herbicide–Resistance Gene bar from *Streptomyces hygroscopicus,"* *EMBO J.*, 6, 2519–2523 (1987).

Tomes, D. "Status of Corn Transformation," 26th Annual Corn Breeders School, Meeting Proceedings, U. Illinois, pp. 7–8 (Feb. 26–27, 1990).

Tomes, D. T., et al., "Transgenic Tobacco Plants and their Progeny Derived by Microprojectile Bombardment of Tobacco Leaves," *Plant Mol. Biol.*, 14, 261–261–268 (Feb. 1990).

Twell, D., et al., "Transient Expression of Chimeric Genes Delivered into Pollen by Microprojectile Bombardment," *Plant Physiol.*, 91, 1271–1274 (1989).

Ulian, E., et al., "Transformation of Plants via the Shoot Apex," *In Vitro Cell. Dev. Biol.*, 9, 951–954 (1988).

Usami, S., et al., "Absence in Monocotyledonous Plants of the Diffusible Plant Factors including T–DNA Circularization and vir Gene Expression in Agrobacterium," *Mol. Gen. Genet.*, 209, 221–226 (1987).

Vain, P., et al., "Osmotic Pretreatment Enhances Particle Bombardment–Mediated Transient and Stable Transformation of Maize," *Plant Cell Rep.*, 12, 84–88 (1993).

Vasil, I. K., "Transgenic Cereals Becoming a Reality," *Bio/Technol.*, 8, 797 (Sep. 1990).

Vasil, I. K., et al., "Culture of Protoplasts Isolated from Embryogenic Cell Suspension Cultures of Sugarcane and Maize," *IAPTC Abstracts*, p. 443 (1986).

Vasil, V., et al., "Isolation and Maintenance of Embryogenic Cell Suspension Cultures of Gramineae," In: *Cell Culture and Somatic Cell Genetics of Plants*, vol. I, Academic Press, pp. 152–158 (1984).

Vasil, V., et al., "Plant Regeneration from Friable Embryonic Callus and Cell Suspension Cultures of *Zea mays L.,"* *J. Plant Physiol.*, 124, 399–408 (1986).

Walbot, V., et al., "Molecular genetics of corn," In: *Corn and Corn Improvements*, 3rd edition, Sprauge, G. F., et al., (eds.), American Soc. Agronomy, Madison, WI, pp. 389–430 (1988).

Waldron, C., et al., "Resistance to Hygromycin B," *Plant Mol. Biol.*, 5, 103–108 (1985).

Walters, D. A., et al., "Transformation and Inheritance of Hygromycin Phosphotransferase Gene in Maize Plants," *Plant Molecular Biol.*, 18, 189–200 (1992).

Wan, Y., et al., "Generation of Large Numbers of Independently Transformed Fertile Barley Plants," *Plant Physiol.*, 104, 37–48 (1994).

Wan, Y., et al., "Maize Transformation and Regeneration of Transgenic Plants by Microprojectile Bombardment of Type I Callus," Abstracts, 35th Annual Maize Genetics Conference, p. 5 (Mar. 18–21, 1993).

Wang, Y., et al., "Characterization of cis–Acting Elements Regulating Transcription from the Promoter of a Constitutively Active Rice Actin Gene," *Mol. Cell. Biol.*, 12, 3399–3406 (1992).

Wang, Y., et al., "Transient Expression of Foreign Genes in Rice, Wheat and Soybean Cells Following Particle Bombardment," *Plant Mol. Biol.*, 11, 433–439 (1988).

Weising, K., et al., "Foreign Genes in Plants: Transfer, Structure, Expression and Applications," *Ann. Rev. Genet.*, 22, 421–478 (1988).

White, J., et al., "A Cassette Containing the bar Gene of *Streptomyces hygroscopicus:* a Selectable Marker for Plant Transformation," *Nuc. Acid. Res.*, 18, 1062 (1989).

Whiteley, H. R., et al., "The Molecular Biology of Parasporal Crystal Body Formation in *Bacillus thuringiensis*, *Ann. Rev. Microbiol.*, 40, 549–576 (1986).

Wong, E. Y., et al., "*Arabidopsis thaliana* Small Subunit Leader and Transit Peptide Enhance the Expression of *Bacillus thuringiensis* Proteins in Transgenic Plants," *Plant Mol. Biol.*, 20, 81–93 (1992).

Yang, H., et al. "Production of Kanamycin Resistant Rice Tissues Following DNA Uptake into Protoplasts," *Plant Cell Rep.* 7, 421 (1988).

Yanisch–Perron, C., et al., "Improved M13 Phage Vectors and Host Strains: Nucleotide Sequences of the M13mp18 and puC19 Vectors," *Gene*, 33, 103–119 (1985).

Yugari, Y., et al., "Coordinated End—Product Inhibition in Lysine Synthesis in *Escherichia coli,"* *Biochem. Biophys. Acta.* 62, 612–614 (1962).

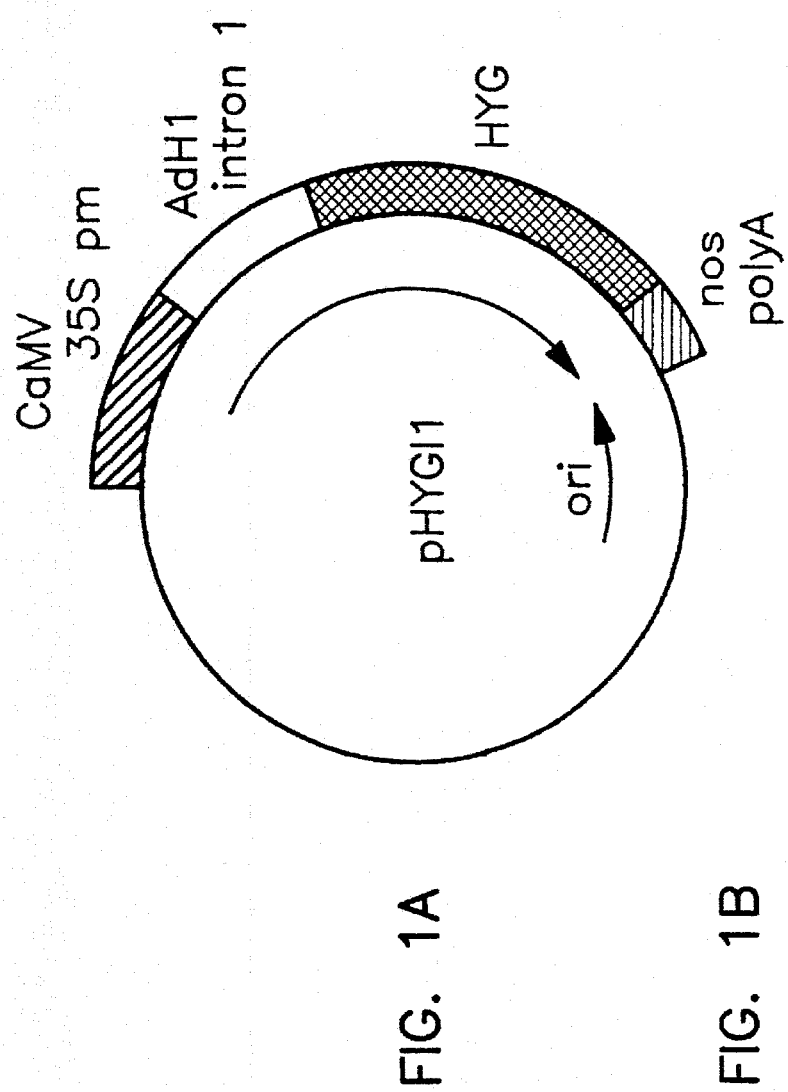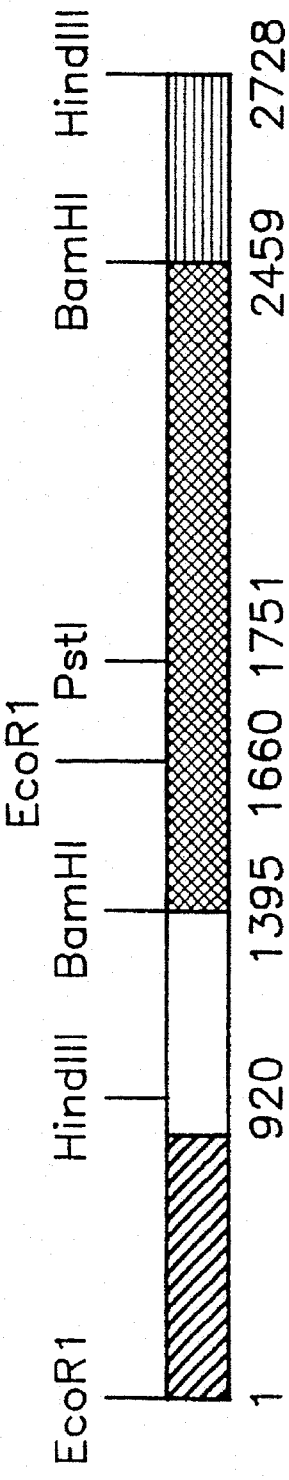
FIG. 1A
FIG. 1B

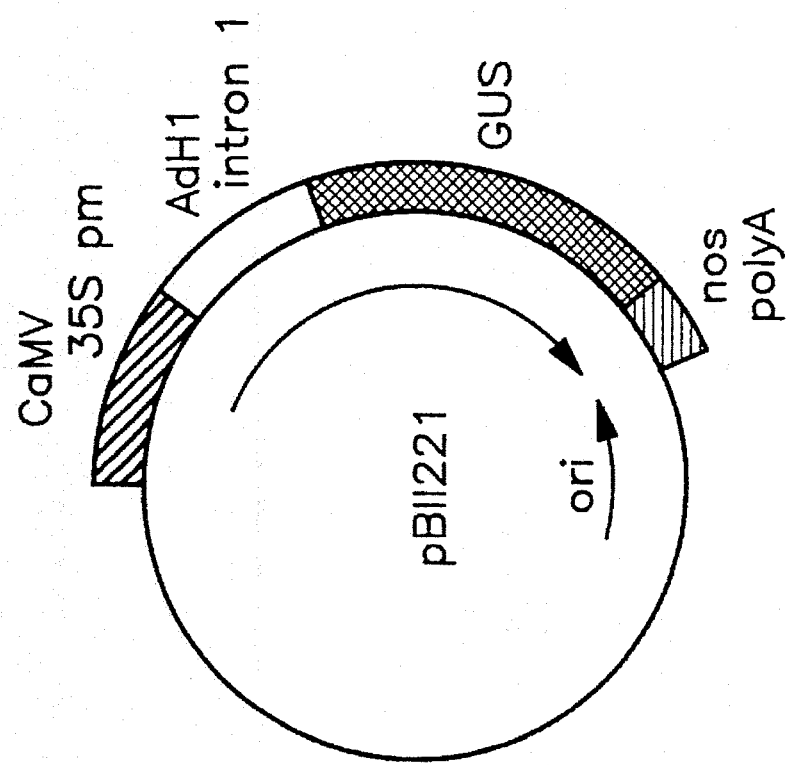
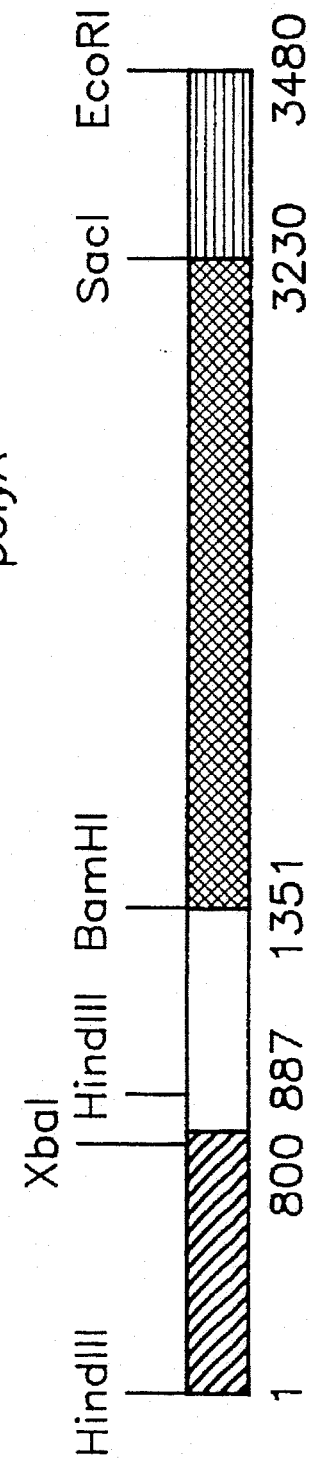
FIG. 2A
FIG. 2B

PHI CALLUS

PHI R₀ PLANTS

PHI R₁ GENERATION

PH2 CALLUS

FERTILE GLYPHOSATE-RESISTANT TRANSGENIC CORN PLANTS

CROSS-REFERENCE TO RELATED APPLICATION

This is a continuation of application Ser. No. 07/508,045, filed Apr. 11, 1990, now U.S. Pat. No. 5,484,956, which is a continuation-in-part of U.S. patent application Ser. No. 07/467,983, filed Jan. 22, 1990, now abandoned.

FIELD OF THE INVENTION

This invention relates to fertile transgenic plants of the species *Zea mays* (oftentimes referred to herein as maize or corn). The invention further relates to producing transgenic plants via particle bombardment and subsequent selection techniques which have been found to produce fertile transgenic plants.

BACKGROUND OF THE INVENTION

Genetic engineering of plants, which entails the isolation and manipulation of genetic material (usually in the form of DNA or RNA) and the subsequent introduction of that genetic material into a plant or plant cells, offers considerable promise to modern agriculture and plant breeding. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques. Once a gene has been identified, cloned, and engineered, it is still necessary to introduce it into a plant of interest in such a manner that the resulting plant is both fertile and capable of passing the gene on to its progeny.

A variety of methods have been developed and are currently available for the transformation of various plants and plant cells with DNA. Generally, these plants have been dicotyledonous, and some success has been reported with certain of the monocotyledonous cereals. However, some species have heretofore proven untransformable by any method. Thus, previous to this discovery, no technology had been developed which would permit the production of stably transformed *Zea mays* plants in which the transforming DNA is heritable thereof. This failure in the art is well documented in the literature and has been discussed in a number of recent reviews (Potrykus, 1989; Weising et al., 1988; Cocking et al., 1987).

European Patent Publications 270,356 (McCabe et al.) and 275,069 (Arntzen et al.) describe the introduction of DNA into maize pollen followed by pollination of maize ears and formation of seeds. The plants germinated from these seeds are alleged to contain the introduced DNA, but there is no suggestion that the introduced DNA was heritable, as has been accomplished in the present invention. Only if the DNA introduced into the corn is heritable can the corn be used in breeding programs as required for successful commercialization of transgenic corn.

Graves et al. (1986) claim Agrobacterium-mediated transformation of *Zea mays* seedlings. The evidence was based upon assays known to be unreliable.

Despite extensive efforts to produce fertile transformed corn plants which transmit the transforming DNA to progeny, there have been no reported successes. Many previous failures have been based upon gene transfer to maize protoplasts, oftentimes derived from callus, liquid suspension culture cells, or other maize cells using a variety of transformation techniques. Although several of the techniques have resulted in successful transformation of corn cells, the resulting cells either could not be regenerated into corn plants or the corn plants produced were sterile (Rhodes et al. 1988) or, in some cases, it even turned out that the plants were, in fact, not transformed. Thus, while maize protoplasts and some other cells have previously been transformed, the resulting transformants could not be regenerated into fertile transgenic plants.

On the other hand, it has been known that at least certain corn callus can be regenerated to form mature plants in a rather straightforward fashion and that the resulting plants are often fertile. However, no stable transformation of maize callus was ever achieved, i.e., there were no techniques developed which would permit a successful stable transformation of a regenerable callus. An example of a maize callus transformation technique which has been tried is the use of Agrobacterium-mediated transfer.

The art was thus faced with a dilemma. While it was known that corn protoplast and suspension culture cells could be transformed, no techniques were available which would regenerate the transformed protoplast into a fertile plant. While it was known that corn callus could be regenerated into a fertile plant, there were no techniques known which could transform the callus, particularly while not destroying the ability of the callus both to regenerate and to form fertile plants.

Recently, a new transformation technique has been created based upon the bombardment of intact cells and tissues with DNA-coated microprojectiles. The technique, disclosed in Sanford et al. (1987) as well as in EPO Patent Publication 331,855 of J. C. Sanford et al. based upon U.S. Ser. No. 07/161,807, filed Feb. 29, 1988, has been shown effective at producing transient gene expression in some plant cells and tissues including those from onion, maize (Klein et al. 1988a), tobacco, rice, wheat, and soybean, and stable expression has been obtained in tobacco and soybeans. In fact, stable expression has been obtained by bombardment of suspension cultures of *Zea mays* Black Mexican Sweet (Klein et al. 1989) which cultures are, however, non-regenerable suspension culture cells, not the callus culture cells used in the process of the present invention.

No protocols have been published describing the introduction of DNA by a bombardment technique into cultures of regenerable maize cells of any type. No stable expression of a gene has been reported by means of bombardment of corn callus followed by regeneration of fertile plants and no regenerable fertile corn has resulted from DNA-coated microprojectile bombardment of the suspension cultures. Thus, the art has failed to produce fertile transformed corn plants heretofore.

A further stumbling block to the successful production of fertile transgenic maize plants has been in selecting those few transformants in such a manner that neither the regeneration capacity nor the fertility of the regenerated transformant are destroyed. Due to the generally low level of transformants produced by a transformation technique, the need for selection of the transformants is self-evident. However, selection generally entails the use of some toxic agent, e.g., herbicide or antibiotic, which may be detrimental to either the regenerability or the resultant plant fertility.

It is thus an object of the present invention to produce fertile, stably transgenic, *Zea mays* plants and seeds which transmit the introduced gene to progeny. It is a further object to produce such stably transgenic plants and seeds by a particle bombardment and a selection process which results in a high level of viability for at least a few transformed cells. It is a further object to produce fertile stably transgenic plants of other graminaceous cereals besides maize.

REFERENCES CITED

The references listed below are incorporated by reference herein.

Armstrong, C. L., et al. (1985) Planta 164:207–214
Callis, J., et al. (1987) Genes & Develop 1:1183–1200
Chilton & Barnes (1983) Nuc Acids Res 11:364–385
Chu, C. C., et al. (1975) Sci Sin (Peking) 18:659–668
Cocking, F., et al. (1987) Science 236:1259–1262
DeWet et al. (1985) Proc Natl Sci USA 82:7870–7873
Freeling, J. C., et al. (1976) Maydica XXI:97–112
Graves, A., et al. (1986) Plant Mol Biol 7:43–50
Green, C., et al. (1975) Crop Sci 15:417–421
Green, C., et al. (1982) Maize for Biological Research, Plant Mol Biol Assoc, pp 367–372
Gritz, L., et al. (1983) Gene 25:179–188
Guilley, H., et al. (1982) Cell 30:763–773
Hallauer, A. R., et al. (1988) Corn and Corn Improvement, 3rd ed., Agronomy Society of America, pp 469–564
Jefferson, R., et al. (1987) EMBO J 6:3901–3907
Kamo, K., et al. (1985) Bot Gaz 146:327–334
Klein, T., et al. (1989) Plant Physiol 91:440–444
Klein, T., et al. (1988a) Proc Natl Acad Sci USA 85:4305–9
Klein, T., et al. (1988b) Bio/Technology 6:559–563
Lu, C., et al. (1982) Theor Appl Genet 62:109–112
McCabe, D., et al. (1988) Bio/Technology 6:923–926
Murashige, T., et al. (1962) Physiol Plant 15:473–497
Neuffer, M., (1982) Maize for Biological Research, Plant Mol Biol Assoc, pp 19–30
Phillips, R., et al. (1988) Corn and Corn Improvement, 3rd ed., Agronomy Society of America, pp 345–387
Potrykus, I. (1989) Trends in Biotechnology 7:269–273
Rhodes, C. A., et al. (1988) Science 240:204–7
Sambrook, J., et al. (1989) Molecular Cloning: A Laboratory Manual, 2nd ed., Cold Spring Harbor Laboratory Press
Sanford, J., et al. (1987) J Part Sci & Techn 5:27–37
Weising, K., et al., (1988) Ann Rev of Genetics 22:421–478
Yanisch-Perron, L., et al. (1985) Gene 33:109–119

SUMMARY OF THE INVENTION

The present invention relates to fertile transgenic *Zea mays* plants containing heterologous DNA, preferably chromosomally integrated heterologous DNA, which is heritable by progeny thereof.

The invention further relates to all products derived from transgenic *Zea mays* plants, plant cells, plant parts, and seeds.

The invention further relates to transgenic *Zea mays* seeds stably containing heterologous DNA and progeny which have inherited the heterologous DNA. The invention further relates to the breeding of transgenic plants and the subsequent incorporation of heterologous DNA into any *Zea mays* plant or line.

The invention further relates to a process for producing fertile transgenic *Zea mays* plants containing heterologous DNA. The process is based upon microprojectile bombardment, selection, plant regeneration, and coventional backcrossing techniques.

The invention further relates to a process for producing fertile transformed plants of graminaceous plants other than *Zea mays* which have not been reliably transformed by traditional methods such as electroporation, Agrobacterium, injection, and previous ballistic techniques.

The invention further relates to regenerated fertile mature maize plants obtained from transformed embryogenic tissue, transgenic seeds produced therefrom, and R1 and subsequent generations.

In preferred embodiments, this invention produces the fertile transgenic plants by means of a DNA-coated microprojectile bombardment of clumps of friable embryogenic callus, followed by a controlled regimen for selection of the transformed callus lines.

BRIEF DESCRIPTION OF THE DRAWINGS

FIG. 1A shows a map of plasmid vector pHYGI1 utilized in Example I. FIG. 1B shows the relevant part of pHYGI1 encompassing the HPT coding sequence and associated regulatory elements. The base pair numbers start from the 5' nucleotide in the recognition sequence for the indicated restriction enzymes, beginning with the EcoRI site at the 5' end of the CaMV 35S promoter.

FIG. 2 shows a map of plasmid vector pBII221 utilized in Example I.

DESCRIPTION OF THE PREFERRED EMBODIMENTS

Figure 3:
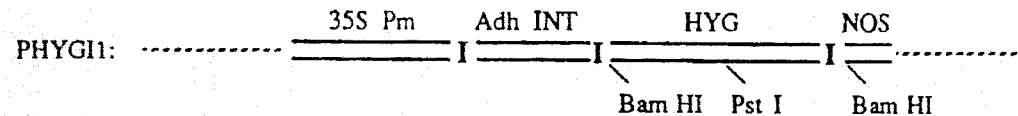
FIG. 3 is a Southern blot of DNA isolated from the PH1 callus line and an untransformed control callus line.
Figure 3:
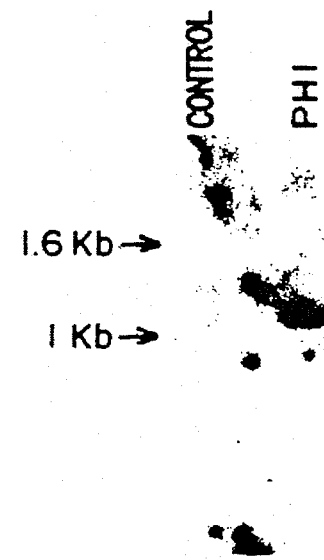

The present invention is directed to the production of fertile transgenic plants and seeds of the species *Zea mays* and to the plants, plant tissues, and seeds derived from such transgenic plants, as well as the subsequent progeny and products derived therefrom. The transgenic plants produced herein include all plants of this species, including field corn, popcorn, sweet corn, flint corn and dent corn.

"Transgenic" is used herein to include any cell, cell line, callus, tissue, plant part or plant, the genotype of which has been altered beneficially by the presence of heterologous DNA that was introduced into the genotype by a process of genetic engineering, or which was initially introduced into the genotype of a parent plant by such a process and is subsequently transferred to later generations by sexual or asexual cell crosses or cell divisions. As used herein, "genotype" refers to the sum total of genetic material within a cell, either chromosomally, or extrachromosomally borne. Therefore, the term "transgenic" as used herein does not encompass the alteration of the genotype of *Zea mays* by conventional plant breeding methods or by naturally occurring events such as random cross-fertilization or spontaneous mutation.

By "heritable" is meant that the DNA is capable of transmission through a complete sexual cycle of a plant, i.e., it is passed from one plant through its gametes to its progeny plants in the same manner as occurs in normal corn.

The transgenic plants of this invention may be produced by (i) establishing a regenerable cell culture, preferably a friable embryogenic callus from the plant to be transformed, (ii) transforming said cell culture by a microprojectile bombardment technique, (iii) controllably identifying or selecting transformed cells, and (iv) regenerating fertile transgenic plants from the transformed cells. Some of the plants of this invention may be produced from the transgenic seed produced from the fertile transgenic plants using conventional crossbreeding techniques to develop transgenic elite lines and varieties, or commercial hybrid seed containing heterologous DNA.

I. Plant Lines and Tissue Cultures

The cells which have been found particularly useful to produce the fertile transgenic maize plants herein are those callus cells which are regenerable, both before and after undergoing a selection regimen as detailed further below. Generally, these cells will be derived from meristematic tissue which contain cells which have not yet terminally differentiated. Such tissue in graminaceous cereals in general and in maize, in particular, comprise tissues found in juvenile leaf basal regions, immature tassels, immature embryos, and coleoptilar nodes. Preferably, immature embryos are used. Methods of preparing and maintaining callus from such tissue and plant types are well known in the art and details on so doing are available in the literature, c.f. Phillips et al. (1988), the disclosure of which is hereby incorporated by reference.

The specific callus used must be able to regenerate into a fertile plant. The specific regeneration capacity of particular callus is important to the success of the bombardment/selection process used herein because during and following selection, regeneration capacity may decrease significantly. It is therefore important to start with cultures that have as high a degree of regeneration capacity as possible. Callus which is more than about 3 months and up to about 36 months of age has been found to have a sufficiently high level of regenerability and thus is preferred. The regenerative capacity of a particular culture may be readily determined by transferring samples thereof to regeneration medium and monitoring the formation of shoots, roots, and plantlets. The relative number of plantlets arising per petri dish or per gram fresh weight of tissue may be used as a rough quantitative estimate of regeneration capacity. Generally, a culture which will produce at least one plant per gram of callus tissue is preferred.

While maize callus cultures can be initiated from a number of different plant tissues, the cultures useful herein are preferably derived from immature maize embryos which are removed from the kernels of an ear when the embryos are about 1–3 mm in length. This length generally occurs about 9–14 days after pollination. Under aseptic conditions, the embryos are placed on conventional solid media with the embryo axis down (scutellum up). Callus tissue appears from the scutellum after several days to a few weeks. After the callus has grown sufficiently, the cell proliferations from the scutellum may be evaluated for friable consistency and the presence of well-defined embryos. By "friable consistency" it is meant that the tissue is easily dispersed without causing injury to the cells. Tissue with this morphology is then transferred to fresh media and subcultured on a routine basis about every two weeks.

The callus initiation media is solid because callus cannot be readily initiated in liquid medium. In preferred embodiments, the initiation/maintenance media is typically based on the N6 salts of Chu et al. (1975) as described in Armstrong et al. (1985) or the MS salts of Murashige et al. (1962). The basal medium is supplemented with sucrose and 2,4-dichlorophenoxyacetic acid (2,4-D). Supplements such as L-proline and casein hydrolysate have been found to improve the frequency of initiation of callus cultures, morphology, and growth. The cultures are generally maintained in the dark, though low light levels may also be used. The level of synthetic hormone 2,4-D, necessary for maintenance and propagation, should be generally about 0.3 to 3.0 mg/l.

Although successful transformation and regeneration has been accomplished herein with friable embryogenic callus, this is not meant to imply that other transformable regenerable cells, tissue, or organs cannot be employed to produce the fertile transgenic plants of this invention. The only actual requirement for the cells which are transformed is that after transformation they must be capable of regeneration of a plant containing the heterologous DNA following the particular selection or screening procedure actually used.

II. DNA Used for Transformation

As used herein, the term "heterologous DNA" refers to a DNA segment that has been derived or isolated from one genotype, preferably amplified and/or chemically altered, and later introduced into a *Zea mays* genotype that may be the same *Zea mays* genotype from which the DNA was first isolated or derived. "Heterologous DNA" also includes completely synthetic DNA, and DNA derived from introduced RNA. Generally, the heterologous DNA is not originally resident in the *Zea mays* genotype which is the recipient of the DNA, but it is within the scope of the invention to isolate a gene from a given *Zea mays* genotype, and to subsequently introduce multiple copies of the gene into the same genotype, e.g., to enhance production of an amino acid.

Therefore, "heterologous DNA" is used herein to include synthetic, semi-synthetic, or biologically derived DNA which is introduced into the *Zea mays* genotype, and retained by the transformed *Zea mays* genotype. The DNA includes but is not limited to, non-plant genes such as those from bacteria, yeasts, animals or viruses; modified genes, portions of genes, chimeric genes, as well as genes from the same or different *Zea mays* genotype.

The heterologous DNA used for transformation herein may be circular or linear, double-stranded or single-stranded. Generally, the DNA is in the form of a plasmid and contains coding regions of beneficial heterologous DNA with flanking regulatory sequences which promote the expression of the heterologous DNA present in the resultant corn plant. For example, the heterologous DNA may itself comprise or consist of a promoter that is active in *Zea mays*, or may utilize a promoter already present in the *Zea mays* genotype that is the transformation target.

The compositions of and method for constructing heterologous DNA which can transform certain plants is well known to those skilled in the art, and the same compositions and methods of construction may be utilized to produce the heterologous DNA useful herein. The specific composition of the DNA is not central to the present invention and the invention is not dependent upon the composition of the specific transforming DNA used. Weising et al. (1988), the subject matter of which is incorporated herein by reference, describes suitable DNA components, which include promoters, polyadenylation sequences, selectable marker genes, reporter genes, enhancers, introns, and the like, as well as provides suitable references for compositions therefrom e.g., on Table 1.

Suitable heterologous DNA for use herein includes all DNA which provides for, or enhances, a beneficial feature of the resultant transgenic corn plant. The DNA may encode proteins or antisense RNA transcripts in order to promote increased food values, higher yields, pest resistance, disease resistance, and the like. For example, the DNA can encode a bacterial dad A for increased lysine production; Bacillus thuringiensis (BT) t-endotoxin or protease inhibitor for insect resistance; bacterial EPSP synthase for resistance to

TABLE 1

Selectable marker and reporter genes in plant genetic transformation

| Gene | Origin | Encoded enzyme | Useful as Selectable marker | Scorable reporter | Resistance against |
|---|---|---|---|---|---|
| Neomycin phosphotransferase gene II (nptII) | Tn5 | neomycin phosphotransferase | ++ | + | neomycin kanamycin G-418[1] |
| Neomycin phosphotransferase gene I (nptI) | Nn601 | neomycin phosphotransferase | + | + | neomycin kanamycin G-418[2] |
| Chloramphenicol acetyltransferase gene (cat) | Tn9 | chloramphenicol acetyltransferase | (+) | ++ | chloramphenicol[3] |
| Bacterial DHFR gene | plasmid R67 | dihydrofolate reductase | + | + | methotrexate[4] |
| Mutated c-DNA of a mouse DHFR gene | mouse | dihydrofolate reductase | ++ | + | methotrexate[5] |
| Octopine synthase gene (ocs) | T-DNA | octopine synthase | + | ++ | toxic opine precursor analogues, i.e. aminoethylcystein[6] |
| Nopaline synthase gene (nos) | T-DNA | nopaline synthase | – | ++ | —[7] |
| Hygromycin phosphotransferase gene (hpt) | E. coli | hygromycin phosphotransferase | ++ | – | hygromycin B[8] |
| Bleomycin resistance gene | Tn5 | ? | + | – | bleomycin[9] |
| Streptomycin phosphotransferase gene | Tn5 | streptomycin phosphotransferase | (+) control plants are not killed by streptomycin | (+) | streptomycin[10] |
| aroA gene | *Salmonella typhimurium* | EPSP synthase | ++ | – | glyphosate[11] |
| bar gene | *Streptomices hygroscopicus* | phosphinothricin acetyltransferase | ++ | – | phosphinothricin, bialophos[12] |
| β-galactosidase gene | E. coli | β-galactosidase | – | + | —[13] |
| Glucuronidase gene (GUS) | E. coli | glucuronidase | – | ++ | —[14] |
| Bacterial luciferase gene | Vibrso harvest | luciferase | – | ++ | —[15] |
| Firefly luciferase gene | *Photonus peralis* | luciferase | – | ++ | —[16] |

Only some representative references were chosen in case of nptII, nos, ocs and cat genes.
Abbreviations
Tn - transpuson
DHFR - dihydrofolate reductase
EPSP synthase - 5-enolpyruvylskikimate-3-phosphate synthase
[1]M. Bevrin et al., Nature, 304, 185 (1983); M. DeBlock et al., EMBO J., 8, 1681 (1984); I. Herrera-Estrella et al., EMBO J., 2, 987 (1983).
[2]R. T. Fraley et al., PNAS USA, 80, 1803 (1983); H. Pretzak et al., Nucl. Acids Res., 14, 5857 (1986).
[3]M. DeBlock et al., EMBO J., 3, 1681 (1984); I. Herrera-Estrella et al., Nature, 303, 209 (1983).
[4]N. Brisson et al., Nature, 310, 511 (1984); M. DeBlock et al., ibid., I. Herrera-Estrella et al., EMBO J., 2, 987 (1983)
[5]D. A. Eichholtz et al., Somat. Cell. Mol. Genet., 13, 67 (1987).
[6]G. A. Dahl et al., Theor. Appl. Genet., 66, 233 (1983); H. De Geve et al., Nature, 300, 752 (1982); A. Hockema et al., Plant Mol. Biol., 5, 85 (1985); M. G. Koztel et al., J. Mol. Appl. Genet., 2, 549 (1981).
[7]J. D. G. Jones et al., EMBO J., 4, 2411 (1985); C. H. Shaw et al., Nuc. Acids Res., 14, 6003 (1986); P. Zambryska et al., EMBO J., 2, 2443 (1983).
[8]A. M. Lloyd et al., Science, 284, 464 (1986); P. I. M. Van den Hazen et al., Plant MOL Biol., 5, 299 (1985); C. Waldron et al., Plant Mol. Biol., 5, 103 (1985).
[9]J. Hille et al., Plant Mol. Biol., 7, 171 (1986).
[10]D. G. Jones et al., Mol. Gen. Genet., 210, 86 (1987).
[11]L. Comai et al., Nature, 317, 741 (1985); J. J. Inllatti et al., Biotechnology, 5, 726 (1987).
[12]M. DeBlock et al., EMBO J., 6, 2513 (1987); C. I. Thompson et al., EMBO J., 6, 2519 (1987).
[13]G. Heimer et al., Biotechnology, 2, 520 (1984).
[14]D. R. Gallic et al., Nuc. Acids Res., 15, 8693 (1987); R. A. Jefferson et al., EMBO J., 6, 1901 (1987).
[15]C. Koncz et al., Mol. Gen. Genet., 204, 383 (1986).
[16]D. W. Ow et al., Science, 234, 856 (1986); D. W. Ow et al., PNAS USA, 84, 4870 (1987); C. D. Riggs et al., Nucl. Acids Res., 15, 8115 (1987).

Sambrook et al. (1989) provides suitable methods of construction.

Generally, the heterologous DNA will be relatively small, i.e., less than about 30 Kb to minimize any susceptibility to physical, chemical, or enzymatic degradation which is known to increase as the size of the DNA increases.

glyphosate herbicide; and chitinase or glucan endo-1,3-B-glucosidase for fungicidal properties. Aside from DNA sequences that serve as transcription units or portions thereof, useful DNA may be untranscribed, serving a regulatory or a structural function. Also, the DNA may be introduced to act as a genetic tool to generate mutants and/or assist in the identification, genetic tagging, or isolation of segments of corn DNA. Additional examples may be found in Weising, supra.

The heterologous DNA to be introduced into the plant further will generally contain either a selectable marker or a reporter gene or both to facilitate identification and selection of transformed cells. Alternatively, the selectable marker may be carried on a separate piece of DNA and used in a co-transformation procedure. Both selectable markers and reporter genes may be flanked with appropriate regulatory sequences to enable expression in plants. Useful selectable markers are well known in the art and include, for example, antibiotic and herbicide resistance genes. Specific examples of such genes are disclosed in Weising et al., supra. A preferred selectable marker gene is the hygromycin B phosphotransferase (HPT) coding sequence, which may be derived from *E. coli* and which confers resistance to the antibiotic hygromycin B. Other selectable markers include aminoglycoside phosphortansferase gene of transposon Tn5 (AphII) which encodes resistance to the antibiotics kanamycin, neomycin, and G418, as well as those genes which code for resistance or tolerance to glyphosate, 1,2-dichloropropionic acid methotrexate, imidazolinones, sulfonylureas, bromoxynil, phosphonothricin and the like. Those selectable marker genes which confer herbicide resistance or tolerance are also of commercial utility in the resulting transformed plants.

Reporter genes which encode for easily assayable marker proteins are well known in the art. In general, a reporter gene is a gene which is not present in or expressed by the recipient organism or tissue and which encodes a protein whose expression is manifested by some easily detectable property, e.g., phenotypic change or enzymatic activity. Examples of such genes are provided in Weising et al., supra. Preferred genes include the chloramphenicol acetyl transferase gene from Tn9 of *E. coli*, the beta-glucuronidase gene of the uidA locus of *E. coli*, and the luciferase genes from firefly *Photinus pyralis*.

The regulatory sequences useful herein include any constitutive, inducible, tissue or organ specific, or developmental stage specific promoter which can be expressed in the particular plant cell. Suitable such promoters are disclosed in Weising et al., supra. The following is a partial representative list of promoters suitable for use herein: regulatory sequences from the T-DNA of *Agrobacterium tumefaciens*, including mannopine synthase, nopaline synthase, and octopine synthase; alcohol dehydrogenase promoter from corn; light inducible promoters such as, ribulose-biphosphate-carboxylase small subunit gene from a variety of species; and the major chlorophyll a/b binding protein gene promoter; 35S and 19S promoters of cauliflower mosaic virus; developmentally regulated promoters such as the waxy, zein, or bronze promoters from maize; as well as synthetic or other natural promoters which are either inducible or constitutive, including those promoters exhibiting organ-specific expression or expression at specific development stage(s) of the plant.

Other elements such as introns, enhancers, polyadenylation sequences and the like, may also be present on the DNA. Such elements may or may not be necessary for the function of the DNA, although they can provide a better expression or functioning of the DNA by affecting transcription, stability of the mRNA, or the like. Such elements may be included in the DNA as desired to obtain the optimal performance of the transforming DNA in the plant. For example, the maize Adh1S first intron may be placed between the promoter and the coding sequence of a particular heterologous DNA. This intron, when included in a DNA construction, is known to generally increase expression of a protein in maize cells. (Callis et al. 1987) However, sufficient expression for a selectable marker to perform satisfactorily can often be obtained without an intron. (Klein et al. 1989) An example of an alternative suitable intron is the *shrunken*-1 first intron of *Zea mays*. These other elements must be compatible with the remainder of the DNA constructions.

To determine whether a particular combination of DNA and recipient plant cells are suitable for use herein, the DNA may include a reporter gene. An assay for expression of the reporter gene may then be performed at a suitable time after the DNA has been introduced into the recipient cells. A preferred such assay entails the use of the *E. coli* beta-glucuronidase (GUS) gene (Jefferson et al. 1987). In the case of the microprojectile bombardment transformation process of the present invention, a suitable time for conducting the assay is about 2–3 days after bombardment. The use of transient assays is particularly important when using DNA components which have not previously been demonstrated or confirmed as compatible with the desired recipient cells.

III. DNA Delivery Process

The DNA can be introduced into the regenerable maize cell cultures, preferably into callus cultures via a particle bombardment process. A general description of a suitable particle bombardment instrument is provided in Sanford et al. (1987), the disclosure of which is incorporated herein by reference. While protocols for the use of the instrument in the bombardment of maize non-regenerable suspension culture cells are described in Klein et al. (1988a, 1988b, and 1989), no protocols have been published for the bombardment of callus cultures or regenerable maize cells.

In a microprojectile bombardment process, also referred to as a biolistic process, the transport of the DNA into the callus is mediated by very small particles of a biologically inert material. When the inert particles are coated with DNA and accelerated to a suitable velocity, one or more of the particles is able to enter into one or more of the cells where the DNA is released from the particle and expressed within the cell. While some of the cells are fatally damaged by the bombardment process, some of the recipient cells do survive, stably retain the introduced DNA, and express it.

The particles, called microprojectiles, are generally of a high density material such as tungsten or gold. They are coated with the DNA of interest. The microprojectiles are then placed onto the surface of a macroprojectile which serves to transfer the motive force from a suitable energy source to the microprojectiles. After the macroprojectile and the microprojectiles are accelerated to the proper velocity, they contact a blocking device which prevents the macroprojectile from continuing its forward path but allows the DNA-coated microprojectiles to continue on and impact the recipient callus cells. Suitable such instruments may use a variety of motive forces such as gunpowder or shock waves from an electric arc discharge (Swain et al. 1988). An instrument in which gunpowder is the motive force is currently preferred and such is described and further explained in Sanford et al. (1987), the disclosure of which is incorporated herein by reference.

A protocol for the use of the gunpowder instrument is provided in Klein et al. (1988a, b) and involves two major steps. First, tungsten microprojectiles are mixed with the DNA, calcium chloride, and spermidine free base in a specified order in an aqueous solution. The concentrations of the various components may be varied as taught. The preferred procedure entails exactly the procedure of Klein et al. (1988b) except for doubling the stated optimum DNA concentration. Secondly, the DNA-coated microprojectiles, macroprojectiles, and recipient cells are placed in position in the instrument and the motive force is applied to the macroprojectiles. Parts of this step which may be varied include the distance of the recipient cells from the end of the barrel as well as the vacuum in the sample chamber. The recipient tissue is positioned 5 cm below the stopping plate tray.

The callus cultures useful herein for generation of transgenic plants should generally be about midway between transfer periods, and thus, past any "lag" phase that might be associated with a transfer to a new media, but also before reaching any "stationary" phase associated with a long time on the same plate. The specific tissue subjected to the bombardment process is preferably taken about 7–10 days after subculture, though this is not believed critical. The tissue should generally be used in the form of pieces of about 30 to 80, preferably about 40 to 60, mg. The clumps are placed on a petri dish or other surface and arranged in essentially any manner, recognizing that (i) the space in the center of the dish will receive the heaviest concentration of metal-DNA particles and the tissue located there is likely to suffer damage during bombardment and, (ii) the number of particles reaching a cell will decrease (probably exponentially) with increasing distance of the cell from the center of the blast so that cells far from the center of the dish are not likely to be bombarded and transformed. A mesh screen, preferably of metal, may be laid on the dish to prevent splashing or ejection of the tissue. The tissue may be bombarded one or more times with the DNA-coated metal particles.

IV. Selection Process

Once the calli have been bombarded with the DNA and the DNA has penetrated some of the cells, it is necessary to identify and select those cells which both contain the heterologous DNA and still retain sufficient regenerative capacity. There are two general approaches which have been found useful for accomplishing this. First, the transformed calli or plants regenerated therefrom can be screened for the presence of the heterologous DNA by various standard methods which could include assays for the expression of reporter genes or assessment of phenotypic effects of the heterologous DNA, if any. Alternatively, and preferably, when a selectable marker gene has been transmitted along with or as part of the heterologous DNA, those cells of the callus which have been transformed can be identified by the use of a selective agent to detect expression of the selectable marker gene.

Selection of the putative transformants is a critical part of the successful transformation process since selection conditions must be chosen so as to allow growth and accumulation of the transformed cells while simultaneously inhibiting the growth of the non-transformed cells. The situation is complicated by the fact that the vitality of individual cells in a population is often highly dependent on the vitality of neighboring cells. Also, the selection conditions must not be so severe that the plant regeneration capacity of the callus cells and the fertility of the resulting plant are precluded. Thus, the effects of the selection agent on cell viability and morphology should be evaluated. This may be accomplished by experimentally producing a growth inhibition curve for the given selective agent and tissue being transformed beforehand. This will establish the concentration range which will inhibit growth.

When a selectable marker gene has been used, the callus clumps may be either allowed to recover from the bombardment on non-selective media, or preferably, directly transferred to media containing that agent.

Selection procedures involve exposure to a toxic agent and may employ sequential changes in the concentration of the agent and multiple rounds of selection. The particular concentrations and cycle lengths are likely to need to be varied for each particular agent. A currently preferred selection procedure entails using an initial selection round at a relatively low toxic agent concentration and then later round(s) at higher concentration(s). This allows the selective agent to exert its toxic effect slowly over a longer period of time. Preferably, the concentration of the agent is initially such that about a 5–40% level of growth inhibition will occur, as determined from a growth inhibition curve. The effect may be to allow the transformed cells to preferentially grow and divide while inhibiting untransformed cells, but not to the extent that growth of the transformed cells is prevented. Once the few individual transformed cells have grown sufficiently, the tissue may be shifted to media containing a higher concentration of the toxic agent to kill essentially all untransformed cells. The shift to the higher concentration also reduces the possibility of non-transformed cells habituating to the agent. The higher level is preferably in the range of about 30 to 100% growth inhibition. The length of the first selection cycle may be from about 1 to 4 weeks, preferably about 2 weeks. Later selection cycles may be from about 1 to about 12 weeks, preferably about 2 to about 10 weeks. Putative maize transformants can generally be identified as proliferating sectors of tissue among a background of non-proliferating cells. The callus may also be cultured on non-selective media at various times during the overall selection procedure.

Once a callus sector is identified as a putative transformant, transformation can be confirmed by phenotypic and/or genotypic analysis. If a selection agent is used, an example of phenotypic analysis is to measure the increase in fresh weight of the putative transformant as compared to a control on various levels of the selective agent. Other analyses that may be employed will depend on the function of the heterologous DNA. For example, if an enzyme or protein is encoded by the DNA, enzymatic or immunological assays specific for the particular enzyme or protein may be used. Other gene products may be assayed by using a suitable bioassay or chemical assay. Other such techniques are well known in the art and are not repeated here. The presence of the gene can also be confirmed by conventional procedures, i.e., Southern blot or polymerase chain reaction (PCR) or the like.

V. Regeneration of Plants and Production of Seed

Cell lines which have been shown to be transformed must then be regenerated into plants and the fertility of the resultant plants determined. Transformed lines which test positive by genotypic and/or phenotypic analysis are then placed on a media which promotes tissue differentiation and plant regeneration. Regeneration may be carried out in accordance with standard procedures well known in the art. The procedures commonly entail reducing the level of auxin which discontinues proliferation of a callus and promotes somatic embryo development or other tissue differentiation. One example of such a regeneration procedure is described in Green et al. (1982). The plants are grown to maturity in a growth room or greenhouse and appropriate sexual crosses and selfs are made as described by Neuffer (1982).

Regeneration, while important to the present invention, may be performed in any conventional manner. If a selectable marker has been transformed into the cells, the selection agent may be incorporated into the regeneration media to further confirm that the regenerated plantlets are transformed. Since regeneration techniques are well known and not critical to the present invention, any technique which accomplishes the regeneration and produces fertile plants may be used.

VI. Analysis of R1 Progeny

The plants regenerated from the transformed callus are referred to as the RO generation or RO plants. The seeds produced by various sexual crosses of the RO generation plants are referred to as R1 progeny or the R1 generation. When R1 seeds are germinated, the resulting plants are also referred to as the R1 generation.

To confirm the successful transmission and inheritance of the heterologous DNA in the sexual crosses described above, the R1 generation should be analyzed to confirm the presence of the transforming DNA. The analysis may be performed in any of the manners such as were disclosed above for analyzing the bombarded callus for evidence of transformation, taking into account the fact that plants and plant parts are being used in place of the callus.

VII. Establishment of the Heterologous DNA in Other Maize Varieties

Fertile, transgenic plants may then be used in a conventional maize breeding program in order to incorporate the introduced heterologous DNA into the desired lines or varieties. Conventional breeding programs employ a conversion process (backcrossing). Methods and references for convergent improvement of corn are given by Hallauer et al., (1988) incorporated herein by reference. Briefly, conversion is performed by crossing the initial transgenic fertile plant to normal elite inbred lines. The progeny from this cross will segregate such that some of the plants will carry the heterologous DNA whereas some will not. The plants that do carry the DNA are then crossed again to the normal plant resulting in progeny which segregate once more. This backcrossing process is repeated until the original normal parent has been converted to a line containing the heterologous DNA and also possessing all other important attributes originally found in the parent. Generally, this will require about 6–8 generations. A separate backcrossing program will be generally used for every elite line that is to be converted to a genetically engineered elite line.

Generally, the commercial value of the transformed corn produced herein will be greatest if the heterologous DNA can be incorporated into many different hybrid combinations. A farmer typically grows several varieties of hybrids based on differences in maturity, standability, and other agronomic traits. Also, the farmer must select a hybrid based upon his physical location since hybrids adapted to one part of the corn belt are generally not adapted to another part because of differences in such traits as maturity, disease, and insect resistance. As such, it is necessary to incorporate the heterologous DNA into a large number of parental lines so that many hybrid combinations can be produced containing the desirable heterologous DNA.

Corn breeding and the techniques and skills required to transfer genes from one line or variety to another are well known to those skilled in the art. Thus, introducing heterologous DNA into other lines or varieties can be readily accomplished by these breeding procedures whether or not they generate the appropriate calli.

VIII. Uses of Transgenic Plants

The transgenic plants produced herein are expected to be useful for a variety of commercial and research purposes. Transgenic plants can be created for use in traditional agriculture to possess traits beneficial to the grower (e.g., agronomic traits such as pest resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes (e.g., Indian corn). Often, chemical constituents (e.g., oils or starches) of corn and other crops are extracted for foods or industrial use and transgenic plants may be created which have enhanced or modified levels of such components. The plants may also be used for seed production for a variety of purposes.

Transgenic plants may also find use in the commercial manufacture of proteins or other molecules encoded by the heterologous DNA contained therein, where the molecule of interest is extracted or purified from plant parts, seeds, and the like. Cells or tissue from the plants may also be cultured, grown in vitro, or fermented to manufacture such molecules, or for other purposes (e.g., for research).

The transgenic plants may also be used in commercial breeding programs, or may be crossed or bred to plants of related crop species. Improvements encoded by the heterologous DNA may be transferred, e.g., from corn cells to cell of other species, e.g., by protoplast fusion.

The transgenic plants may have many uses in research or breeding, including creation of new mutant plants through insertional mutagenesis, in order to identify beneficial mutants that might later be created by traditional mutation and selection. The methods of the invention may also be used to create plants having unique "signature sequences" or other marker sequences which can be used to identify proprietary lines or varieties.

The following non-limiting examples are illustrative of the present invention. They are presented to better explain the general procedures which were used to prepare the fertile Zea mays plants of this invention which stably express the heterologous DNA and which transmit that DNA to progeny. All parts and percents are by weight unless otherwise specified. It must be recognized that a specific transformation event is a function of the amount of material subjected to the transformation procedure. Thus, when individual situations arise in which the procedures described herein do not produce a transformed product, repetition of the procedures will be required.

EXAMPLE I.

Fertile transgenic Zea mays plants which contain heterologous DNA which is heritable were prepared as follows:

I. Initiation and maintenance of maize cell cultures which retain plant regeneration capacity Friable, embryogenic maize callus cultures were initiated from hybrid immature embryos produced by pollination of inbred line A188 plants (University of Minnesota, Crop Improvement Association) with pollen of inbred line B73 plants (Iowa State University). Ears were harvested when the embryos had reached a length of 1.5 to 2.0 mm. The whole ear was surface sterilized in 50% v/v commercial bleach (2.63% w/v sodium hypochlorite) for 20 min. at room temperature. The ears were then washed with sterile, distilled, deionized water. Immature embryos were aseptically isolated and placed on nutrient medium initiation/maintenance media with the root/shoot axis exposed to the medium. Initiation/maintenance media (hereinafter referred to as "F medium") consisted of N6 basal media (Chu 1975) with 2% (w/v) sucrose, 1.5 mg per liter 2,4-dichlorophenoxyacetic acid (2,4-D), 6 mM proline, and 0.25% Gelrite (Kelco, Inc., San Diego). The pH was adjusted to 5.8 prior to autoclaving. Unless otherwise stated, all tissue culture manipulations were carried out under sterile conditions.

The immature embryos were incubated at 26° C. in the dark. Cell proliferations from the scutellum of the immature embryos were evaluated for friable consistency and the presence of well-defined somatic embryos. Tissue with this morphology was transferred to fresh media 10 to 14 days after the initial plating of the immature embryos. The tissue was then subcultured on a routine basis every 14 to 21 days. Sixty to eighty milligram quantities of tissue were removed from pieces of tissue that had reached a size of approximately one gram and transferred to fresh media. Subculturing always involved careful visual monitoring to be sure that only tissue of the correct morphology was maintained. The presence of somatic embryos ensured that the cultures would give rise to plants under the proper conditions. The cell culture named AB12 used in this example was such a culture and had been initiated about 1 year before bombardment.

II. Plasmids—pCHN1-1, pHYGI1, pBII221, and pLUC-1

The plasmids pCHN1-1, pHYGI1, and pLUC-1 were constructed in the vector pBS+ (Stratagene, Inc., San Diego, Calif.), a 3.2 Kb circular plasmid, using standard recombinant DNA techniques. pCHN1-1 contains the hygromycin B phosphotransferase (HPT) coding sequence from *E. coli* (Gritz et al. 1983) flanked at the 3' end by the nopaline synthase (nos) polyadenylation sequence of *Agrobacterium tumefaciens* (Chilton and Barnes 1983). Expression is driven by the cauliflower mosaic virus (CaMV) 35S promoter (Guilley et al. 1982), located upstream from the hygromycin coding sequence. The plasmid pHYGI1 was constructed by inserting the 553 bp Bcl-BamHI fragment containing the maize AdhIS first intron (Callis et al. 1987) between the CaMV 35S promoter and the hygromycin coding sequence of pCHN1-1. A map of pHYGI1 is provided as FIG. 1. A sample of pHYGI1 was deposited at the American Type Culture Collection, Rockville, Md., U.S.A., on Mar. 16, 1990, under the provisions of the Budapest Treaty, and assigned accession number 40774.

pBII221 contains the *E. coli* B-glucuronidase coding sequence flanked at the 5' end by the CaMV 35S promoter and at the 3' end by the nos polyadenylation sequence. The plasmid was constructed by inserting the maize AdhIS first intron between the 35S promoter and the coding sequence of pBI221 (Jefferson et al. 1987). A map of pBII221 is provided as FIG. 2.

pLUC-1 contains the firefly luciferase coding sequence (DeWet et al. 1987) flanked at the 5' end by the CaMV 35S promoter and at the 3' end by the nos polyadenylation sequence. This plasmid was used solely as negative control DNA.

Plasmids were introduced into the embryogenic callus culture AB12 by microprojectile bombardment.

III. DNA delivery process

The embryogenic maize callus line AB12 was subcultured 7 to 12 days prior to microprojectile bombardment. AB12 was prepared for bombardment as follows. Five clumps of callus, each approximately 50 mg in wet weight were arranged in a cross pattern in the center of a sterile 60×15 mm petri plate (Falcon 1007). Plates were stored in a closed container with moist paper towels, throughout the bombardment process. Twenty-six plates were prepared.

Plasmids were coated onto M-10 tungsten particles (Biolistics) exactly as described by Klein et al. (1988b) except that, (i) twice the recommended quantity of DNA was used, (ii) the DNA precipitation onto the particles was performed at 0° C., and (iii) the tubes containing the DNA-coated tungsten particles were stored on ice throughout the bombardment process.

All of the tubes contained 25 µl 50 mg/ml M-10 tungsten in water, 25 µl 2.5M CaCl$_2$, and 10 µl 100 mM spermidine free base along with a total of 5 µl 1 mg/ml total plasmid content. When two plasmids were used simultaneously, each was present in an amount of 2.5 µl. One tube contained only plasmid pBII221; two tubes contained both plasmids pHYGI1 and pBII221; two tubes contained both plasmids pCHN1-1 and pBII221; and one rude contained only plasmid pLUC-1.

All tubes were incubated on ice for 10 min., pelletized by centrifugation in an Eppendorf centrifuge at room temperature for 5 seconds, and 25 µl of the supernatant was discarded. The tubes were stored on ice throughout the bombardment process. Each preparation was used for no more than 5 bombardments.

Macroprojectiles and stopping plates were obtained from Biolistics, Inc. (Ithaca, N.Y.). They were sterilized as described by the supplier. The microprojectile bombardment instrument was obtained from Biolistics, Inc.

The sample plate tray was positioned at the position 5 cm below the bottom of the stopping plate tray of the microprojectile instrument, with the stopping plate in the slot nearest to the barrel. Plates of callus tissue prepared as described above were centered on the sample plate tray and the petri dish lid removed. A 7×7 cm square rigid wire mesh with 3×3 mm mesh and made of galvanized steel was placed over the open dish in order to retain the tissue during the bombardment. Tungsten/DNA preparation were sonicated as described by Biolistics, Inc. and 2.5 µl was pipetted onto the top of the macroprojectiles. The instrument was operated as described by the manufacturer. The bombardments which were performed are summarized on Table 2.

TABLE 2

| | |
|---|---|
| 2 × pBII221 prep | To determine transient expression frequency |
| 10 × pHYGI1/pBII221 | As a potential positive treatment for transformation |
| 10 × pCHN1-1/pBII221 | As a potential positive treatment for transformation |
| 4 × pLUC-1 | Negative control treatment |

The two plates of callus bombarded with pBII221 were transferred plate for plate to F medium (with no hygromycin) and the callus cultured at 26° C. in the dark. After 2 days, this callus was then transferred plate for plate into 35×10 mm petri plates (Falcon 1008) containing 2 ml of GUS assay buffer which consists of 1 mg/ml 5-bromo-4-chloro-3-indolyl-beta-D-glucuronide (Research Organics), 100 mM sodium phosphate pH 7.0, 5 mM each of potassium ferricyanide and potassium ferrocyanide, 10 mM EDTA, and 0.06% Triton X-100. These were incubated at 37° C. for 3 days later which the number of blue cells was counted giving 291 and 477 transient GUS expressing cells in the two plates, suggesting that the DNA delivery process had also occurred with the other bombarded plates. These plates were discarded after counting since the GUS assay is destructive.

IV. Selection process

Hygromycin a (Calbiochem) was incorporated into the medium by addition of the appropriate volume of filter sterilized 100 mg/ml hygromycin B in water when the media had cooled to 45° C. prior to pouring plates.

Immediately after all samples had been bombarded, callus from all of the plates treated with pHYGI1/pBII221, pCHN1-1/pBII221 and three of the plates treated with pLUC-1 were transferred plate for plate onto F medium containing 15 mg/l hygromycin B, (five pieces of callus per plate). These are referred no as round 1 selection plates. Callus from the fourth plate treated with pLUC-1 was transferred to F medium without hygromycin. This tissue was subcultured every 2–3 weeks onto nonselective medium and is referred to as unselected control callus.

After two weeks of selection, tissue appeared essentially identical on both selective and nonselective media. All callus from eight plates from each of the pHYGI1/pBII221 and pCHN1-1/pBII221 treatments and two plates of the control callus on selective media were transferred from round 1 selection plates to round 2 selection plates that contained 60 mg/l hygromycin. The round 2 selection plates each contained ten 30 mg pieces of callus per plate, resulting in an expansion of the total number of plates.

The remaining tissue on selective media, two plates each of pHYGI1/pBII221 and pCHN1-1/pBII221 treated tissue and one of control callus, were placed in GUS assay buffer at 37° C. to determine whether blue clusters of cells were observable at two weeks post-bombardment. After 6 days in assay buffer, this tissue was scored for GUS expression. The results are summarized on Table 3.

TABLE 3

| Treatment | Replicate | Observations |
| --- | --- | --- |
| pLUC-1 | | No blue cells |
| pHYGI1/pBII221 | Plate 1 | 11 single cells |
| | | 1 four-cell cluster |
| | Plate 2 | 5 single cells |
| pCHN1-1/pBII221 | Plate 1 | 1 single cell |
| | | 2 two-cell clusters |
| | Plate 2 | 5 single cells |
| | | 1 two-cell cluster |
| | | 2 clusters of 8–10 cells |

After 21 days on the round 2 selection plates, all viable portions of the material were transferred to round 3 selection plates containing 60 mg/l hygromycin. The round 2 selection plates, containing only tissue that was apparently dead, were reserved. Both round 2 and 3 selection plates were observed periodically for viable proliferating sectors.

After 35 days on round 3 selection plates, both the round 2 and round 3 sets of selection plates were checked for viable sectors of callus. Two such sectors were observed proliferating from a background of dead tissue on plates treated with pHYGI1/pBII221. The first sector named 3AA was from the round 3 group of plates and the second sector named 6L was from the round 2 group of plates. Both lines were then transferred to F medium without hygromycin.

After 19 days on F medium without hygromycin, the line 3AA grew very little whereas the line 6L grew rapidly. Both were transferred again to F medium for 9 days. The lines 3AA and 6L were then transferred to F medium containing 15 mg/l hygromycin for 14 days. At this point, line 3AA was observed to be of very poor quality and slow growing. The line 6L, however, grew rapidly on F medium with 15 mg/l hygromycin; the line was then subcultured to F medium without hygromycin.

After 10 days on F medium, an inhibition study of the line 6L was initiated. Callus of 6L was transferred onto F medium containing 1, 10, 30, 100, and 250 mg/l hygromycin B. Five plates of callus were prepared for each concentration and each plate contained ten approximately 50 mg pieces of callus. One plate of unselected control tissue was prepared for each concentration of hygromycin.

It was found that the line 6L was capable of sustained growth over 9 subcultures on 0, 10, 30, 100, and 250 mg/l hygromycin. The name of the line 6L was changed at this time from 6L to PH1 (Positive Hygromycin transformant 1).

Additional sectors were recovered at various time points from the round 2 and 3 selection plates. None of these were able to grow in the presence of hygromycin for multiple rounds, i.e., two or three subcultures.

V. Confirmation of transformed callus

To show that the PH1 callus had acquired the hygromycin resistance gene, a Southern blot of PH1 callus was prepared as follows: DNA was isolated from PH1 and unselected control calli by freezing 2 g of callus in liquid nitrogen and grinding it to a fine powder which was transferred to a 30 ml Oak Ridge tube containing 6 ml extraction buffer (7M urea, 250 mM NaCl, 50 mM Tris-HCl pH 8.0, 20 mM EDTA pH 8.0, 1% sarcosine). To this was added 7 ml of phenol:chloroform 1:1, the tubes shaken and incubated at 37° C. 15 min. Samples were centrifuged at 8K for 10 min. at 4° C. The supernatant was pipetted through miracloth (Calbiochem 475855) into a disposable 15 ml tube (American Scientific Products, C3920-15A) containing 1 ml 4.4M ammonium acetate, pH 5.2. Isopropanol, 6 ml was added, the tubes shaken, and the samples incubated at −20° C. for 15 min. The DNA was pelleted in a Backman TJ-6 centrifuge at the maximum speed for 5 min. at 4° C. The supernatant was discarded and the pellet was dissolved in 500 µl TE-10 (10 mM Tris-HCl pH 8.0, 10 mM EDTA pH 8.0) 15 min. at room temperature. The samples were transferred to a 1.5 ml Eppendorf tube and 100 µl 4.4M ammonium acetate, pH 5.2 and 700 µl isopropanol were added. This was incubated at −20° C. for 15 min. and the DNA pelleted 5 min. in an Eppendorf microcentrifuge (12,000 rpm). The pellet was washed with 70% ethanol, dried, and resuspended in TE-1 (10 mM Tris-HCl pH 8.0, 1 mM EDTA).

The isolated DNA (10 µg) was digested with BamHI (NEB) and electrophoresed in a 0.8% w/v agarose gel at 15 V for 16 hrs in TAE buffer (40 mM Tris-acetate, 1 mM EDTA). The DNA within the gel was then depurinated by soaking the gel twice in 0.25 HCl for 15 min., denatured and cleaved by soaking the get twice in 0.5M NaOH/1.0M NaCl 15 min., and neutralized by soaking the gel twice in 0.5M Tris pH 7.4/3 M NaCl 30 min. DNA was then blotted onto a Nytran membrane (Shleicher & Shuell) by capillary transfer overnight in 6× SSC (20× SSC, 3M NaCl, 0.3M sodium citrate pH 7.0). The membrane was baked at 80° C. for 2 hrs under vacuum. Prehybridization treatment of the membrane was done in 6× SSC, 10× Denhardt's solution, 1% SDS, 50 µg/ml denatured salmon sperm DNA using 0.25 ml prehybridization solution per $cm^2$ of membrane. Prehybridization was carried out at 42° C. overnight.

A $^{32}P$ labelled probe was prepared by random primer labelling with an Oligo Labelling Kit (Pharmacia) as per the supplier's instructions with $^{32}P$-dCTP (ICN Radiochemicals). The template DNA used was the 1055 bp BamHI fragment of pHYGI1, which is the HPT coding sequence. The fragment was gel purified and cut again with PstI (NEB) before labelling.

The hybridization was performed in 50% formamide, 6× SSC, 1% SDS, 50 µ/ml denatured salmon sperm DNA (Sigma), 0.05% sodium pyrophosphate and all of the isopropanol precipitated heat denatured probe ($10^7$ CPM/50 ng template). The hybridization was carried out at 42° C. overnight.

The membrane was washed twice in 50 ml 6× SSC, 0.1% SDS 5 min. at room temperature with shaking, then twice in 500 ml 6× SSC, 0.1% SDS 15 min at room temperature, then twice in 500 ml 1× SSC, 1% SDS 30 min at 42° C., and finally in 500 ml 0.1× SSC, 1% SDS 60 min. at 65° C. Membranes were exposed to Kodak X-OMAT AR film in an X-OMATIC cassette with intensifying screens. As shown in FIG. 3, a band was observed for PH1 callus at the expected position of 1.05 Kb, indicating that the HPT coding sequence was present. No band was observed for control callus.

To demonstrate that the hygromycin gene is incorporated into high molecular weight DNA, DNA isolated from PH1 callus and control callus was treated with (i) no restriction enzyme, (ii) BamHI, as described previously, or (iii) PstI, which cuts the plasmid pHYGI1 only once within the HPT coding sequence. Samples were blotted and probed with the HPT coding sequence as described previously.

Undigested PH1 DNA only showed hybridization to the probe at the position of uncut DNA, demonstrating that the hygromycin gene is incorporated into high molecular weight DNA. The expected 1.05 Kb band for PH1 DNA digested with BamHi was observed, as had been shown previously. For PH1 DNA digested with PstI, a 5.9 Kb band would be expected if the hygromycin gene was present on an intact pHYGI1 plasmid. Two or more bands of variable size (size dependent on the position flanking PstI sites within the host DNA would be expected if the gene was incorporated into high molecular weight DNA. Three bands were observed with approximate molecular sizes of 12, 5.1, and 4.9 Kb. This result demonstrates incorporation of the hygromycin gene into high molecular weight DNA. The intensity of the 4.9 Kb band is approximately twice as great as the other two bands, suggesting either partial digestion or possibly a tandem repeat of the HPT gene. No hybridization was observed for DNA from control callus in any of the above treatments.

These results prove that the HPT coding sequence is not present in PH1 callus as intact pHYGI1 or as a small non-chromosomal plasmid. They are consistent with incorporation of the hygromycin gone into high molecular weight DNA.

VI. Plant regeneration and production of seed

PH1 callus was transferred directly from all of the concentrations of hygromycin used in the inhibition study to RM5 medium which consists of MS basal salts (Murashige et al. 1962) supplemented with thiamine.HCl 0.5 mg/l, 2,4-D 0.75 mg/l sucrose 50 g/l, asparagine 150 mg/l, and Gelrite 2.5 g/l (Kelco Inc., San Diego).

After 14 days on RM5 medium, the majority of PH1 and negative control callus was transferred to R5 medium which is the same as RM5 medium, except that 2,4-D omitted. These were cultured in the dark for 7 days at 26° C. and transferred to a light regime of 14 hrs light and 10 hrs dark for 14 days at 26° C. At this point, plantlets that had formed were transferred to one quart canning jars (Ball) containing 100 ml of R5 medium. Plants were transferred from jars to vermiculite for 7 or 8 days before transplanting then into soil and growing them to maturity. A total of 65 plants were produced from PH1 and a total of 30 plants were produced from control callus.

Figure 4:
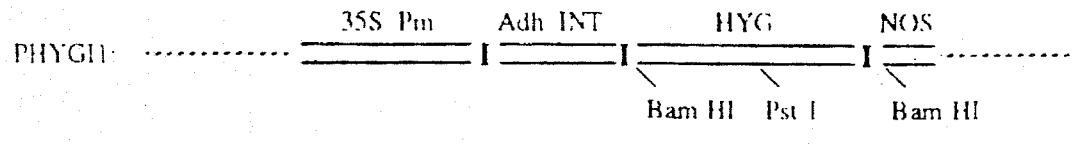
FIG. 4 is a Southern blot of leaf DNA isolated from Ro plants regenerated from PH1 and untransformed callus.
Figure 4:
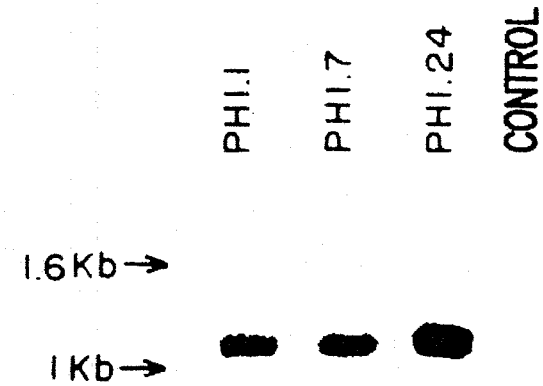

To demonstrate that the introduced DNA had been retained in the Ro tissue, a Southern blot was performed as previously described on BamHI digested leaf DNA from three randomly chosen Ro plants of PH1. As shown in FIG. 4, a 1.05 Kb band was observed with all three plants indicating that the HPT coding sequence was present. No band was observed for DNA from a control plant.

Controlled pollinations of mature PH1 plants were conducted by standard techniques with inbred *Zea mays* lines A188, B73, and Oh43. Seed was harvested 45 days postpollination and allowed to dry further 1–2 weeks. Seed set varied from 0 to 40 seeds per ear when PH1 was the female parent and 0 to 32 seeds per ear when PH1 was the male parent.

VII. Analysis of the R1 progeny

The presence of the hygromycin resistance trait was evaluated by a root elongation bioassay, an etiolated leaf bioassay, and by Southern blotting. Two ears each from regenerated PH1 and control plants were selected for analysis. The pollen donor was inbred line A188 for all ears.

A. Root elongation bioassay

Seed was sterilized in a 1:1 dilution of commercial bleach in water plus alconox 0.1% for 20 min. in 125 ml Erlenmyer flasks and rinsed 3 times in sterile water and inbibed overnight in sterile water containing 50 mg/ml captan by shaking at 150 rpm.

After imbibition, the solution was decanted from the flasks and the seed transferred to flow boxes (Flow Laboratories) containing 3 sheets of $H_2O$ saturated germination paper. A fourth sheet of water saturated germination paper was placed on top of the seed. Seed was allowed to germinate 4 days.

After the seed had germinated, approximately 1 cm of the primary root tip was excised from each seedling and plated on MS salts, 20 g/l sucrose, 50 mg/l hygromycin, 0.25% Gelrite, and incubated in the dark at 26° C. for 4 days.

Roots were evaluated for the presence or absence of abundant root hairs and root branches. Roots were classified as transgenic (hygromycin resistant) if they had root hairs and root branches, and untransformed (hygromycin sensitive) if they had limited numbers of branches. The results are shown in Table 3, hereinbelow.

B. Etiolated leaf bioassay

After the root tips were excised as described above, the seedlings of one PH1 ear and one control ear were transferred to moist vermiculite and grown in the dark for 5 days.

At this point, 1 mm sections were cut from the tip of the coleoptile, surface sterilized 10 seconds, and plated on MS basal salts, 20 g/l sucrose, 2.5 g/l Gelrite with either 0 (control) or 100 mg/l hygromycin and incubated in the dark at 26° C. for 18 hrs. Each plate contained duplicate sections of each shoot. They were then incubated in a light regimen of 14 hrs light 10 hrs dark at 26° C. for 48 hrs, and rated on a scale of from 0 (all brown) to 6 (all green) for the percent of green color in the leaf tissue. Shoots were classified as untransformed (hygromycin sensitive) if they had a rating of zero and classified as transformed (hygromycin resistant) if they had a rating of 3 or greater. The results are shown in Table 1, hereinbelow.

C. Southern blots

Figure 5:
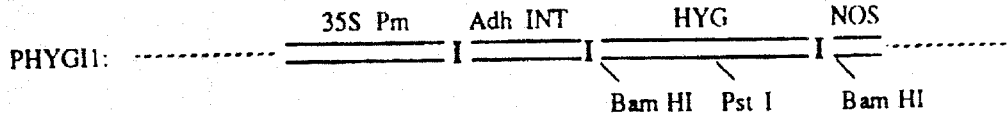
FIG. 5 is a Southern blot of leaf DNA isolated from R1 progeny of PH1 Ro plants and untransformed Ro plants.

Seedlings from the bioassays were transplanted to soil and were grown to sexual maturity. DNA was isolated from 0.8 g of leaf tissue about 3 weeks after transplanting to soil and probed with the HPT coding sequence as described previously. Plants with a 1.05 Kb band present in the Southern blot were classified as transgenic. As shown in FIG. 5, two out of seven progeny of PH1 plant 3 were transgenic as were three out of eight progeny of PH1 plant 10. The blot results correlated precisely with data from the bioassays, confirming that the heterologous DNA was transmitted through one complete sexual life cycle. All data are summarized in Table 4.

All of the tubes contained 25 µl 50 mg/ml M-10 tungsten in water, 25 µl 2.5M $CaCl_2$, and 10 µl 100 mM spermidine free base along with a total of 5 µl 1 mg/ml total plasmid content. One tube contained only plasmid pBII221; two tubes contained only plasmid pHYGI1; and one tube contained no plasmid but 5 µl TE-1 (10 mM Tris-HCl pH 8.0, 1 mM EDTA pH 8.0).

The following bombardments were done: 2×pBII221 prep (for transient expression); 7×pHYGI1 prep (potential positive treatment); and 3×TE prep (negative control treatment).

After all the bombardments were performed, the callus from the pBII221 treatment was transferred plate for plate to F medium as five 50 mg pieces. After 2 days, the callus was placed into GUS assay buffer as per Example I. Numbers of transiently expressing cells were counted and found to be 686 and 845 GUS positive cells, suggesting that the particle delivery process had occurred in the other bombarded plates.

IV. Selection of Transformed Callus

After bombardment, the callus from the pHYGI1 treatments was placed onto round 1 selection plates, F medium containing 15 mg/l hygromycin, as ten 25 mg pieces per plate (different from Example I). The same was done for two of the plates bombarded with the TE preparation (selected control callus). One plate of callus bombarded with the TE preparation was placed onto F medium with no hygromycin;

TABLE 4

| | | ANALYSIS OF PH1 R1 PLANTS | | | | | |
|---|---|---|---|---|---|---|---|
| PH1 PLANT | ROOT ASSAY | LEAF ASSAY | BLOT | CONT PLANT | ROOT ASSAY | LEAF ASSAY | BLOT |
| 3.1 | + | ND | + | 4.1 | − | ND | ND |
| 3.2 | − | ND | − | 4.2 | − | ND | ND |
| 3.3 | − | ND | − | 4.3 | − | ND | ND |
| 3.4 | − | ND | − | 4.4 | − | ND | ND |
| 3.5 | − | ND | − | 4.5 | − | ND | ND |
| 3.6 | + | ND | + | 4.6 | − | ND | ND |
| 3.7 | − | ND | − | 4.7 | − | ND | ND |
| | | | | 2.1 | − | ND | − |
| 10.1 | + | + | + | 1.1 | − | − | − |
| 10.2 | + | + | + | 1.2 | − | − | ND |
| 10.3 | − | − | ND | 1.3 | − | − | ND |
| 10.4 | − | − | − | 1.4 | − | − | ND |
| 10.5 | − | − | − | 1.5 | − | − | ND |
| 10.6 | − | − | − | 1.6 | − | − | ND |
| 10.7 | − | − | − | 1.7 | − | − | ND |
| 10.8 | ND | + | + | 1.8 | − | − | ND |

Key: + transgenic; − = nontransgenic; ND = not done

EXAMPLE II

The procedure of Example I was repeated with minor modifications.

I. Plant Lines and Tissue Cultures

The embryogenic maize callus line, AB12, was used as in Example I. The line had been initiated about 18 months before the actual bombardment occurred.

II. Plasmids

The plasmids pBII221 and pHYGI1 described in Example I were used.

III. DNA Delivery Process

Callus was bombarded exactly as in Example I except that the DNA used in the tungsten/DNA preparations differed.

this callus was maintained throughout the ongoing experiment as a source of control tissue (unselected control callus).

After 13 days, the callus on round 1 selection plates was indistinguishable from unselected control callus. All of the callus was transferred from round 1 selection plates to round 2 selection plates containing 60 mg/l hygromycin. An approximate five-fold expansion of the numbers of plates occurred.

The callus on round 2 selection plates had increased substantially in weight after 23 days, but at this time appeared close to dead. All of the callus was transferred from round 2 selection plates to round 3 selection plates containing 60 mg/l hygromycin. This transfer of all material from round 2 to round 3 selection differs from Example I in which only viable sectors were transferred and the round 2 plates reserved.

At 58 days post-bombardment, three live sectors were observed proliferating from the surrounding dead tissue. All three lines were from pHYGI1 treatments and were designated 24C, 56A, and 55A.

After 15 days on maintenance medium, growth of the lines was observed. The line 24C grew well whereas lines 55A and 56A grew more slowly. All three lines were transferred to F medium containing 60 mg/l hygromycin. Unselected control callus from maintenance medium was plated to F medium having 60 mg/l hygromycin.

After 19 days on 60 mg/l hygromycin, the growth of line 24C appeared to be entirely uninhibited, with the control showing approximately 80% of the weight gain of 24C. The line 56A was completely dead, and the line 55A was very close to dead. The lines 24C and 55A were transferred again to F 60 mg/l hygromycin as was the control tissue.

After 23 days on 60 mg/l hygromycin, the line 24C again appeared entirely uninhibited. The line 55A was completely dead, as was the negative control callus on its second exposure to F medium having 60 mg/l hygromycin.

At 88 days post-bombardment, a sector was observed proliferating among the surrounding dead tissue on the round 3 selection plates. The callus was from a plate bombarded with pHYGI1 and was designated 13E. The callus was transferred to F medium and cultured for 19 days. Portions of the callus were then transferred to (i) F media containing 15 mg/l hygromycin, and (ii) F medium containing 60 mg/l hygromycin. Control callus was plated on F media with 15 mg/l hygromycin. After 14 days of culture, the callus line 13E appeared uninhibited on both levels of hygromycin. The control callus appeared to have about 80% of the weight gain of 13E. The callus lines were transferred to fresh media at the same respective levels of hygromycin.

V. Confirmation of Transformed Callus

Figure 6:
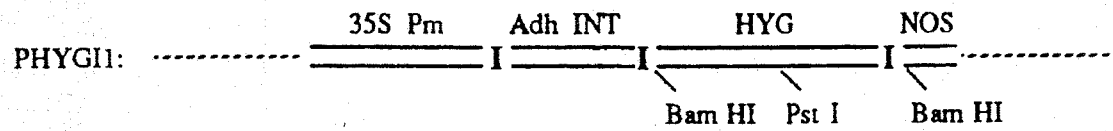
FIG. 6 is a Southern blot of DNA isolated from the PH2 callus line and an untransformed control callus line.
Figure 6:
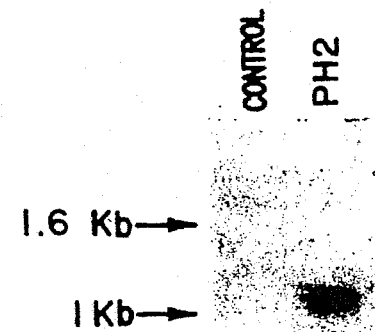

A Southern blot was prepared from BamHI-digested DNA from the line 24C. As shown in FIG. 6, a band was observed for the line 24C at the expected size of 1.05 Kb showing that the line 24C contained the HPT coding sequence. No band was observed for DNA from control tissue. The name of the callus line 24C was changed to PH2.

To demonstrate that the hygromycin gene is incorporated into high molecular weight DNA, DNA isolated from PH2 callus and control callus was treated with (i) no restriction enzyme, (ii) BamHI, as described previously, or, (iii) PstI, which cuts the plasmid pHYGI1 only once within the HPT coding sequence. Samples were blotted and probed with the HPT coding sequence as described previously.

Undigested PH2 DNA only showed hybridization to the probe at the position of uncut DNA, demonstrating that the hygromycin gene is incorporated into high molecular weight DNA. The expected 1.05 Kb band for PH2 DNA digested with BamHI was observed, as had been shown previously. For PH2 DNA digested with PstI, a 5.9 Kb band would be expected if the hygromycin gene was present on an intact pHYGI1 plasmid. Two or more bands of variable size (size dependent on the position of flanking PstI sites within the host DNA) would be expected if the gene was incorporated into high molecular weight DNA. Two bands were observed with approximate molecular sizes of 6.0 and 3.0 Kb. This result is consistent with incorporation of the hygromycin gene into high molecular weight DNA. No hybridization was observed for DNA from control callus in any of the above treatments.

These results prove that the HPT coding sequence is not present in PH2 callus as intact pHYGI1 or as a small non-chromosomal plasmid. They are consistent with incorporation of the hygromycin gene into high molecular weight DNA.

VI. Plant Regeneration and Production of Seed

The line PH2, along with unselected control callus, were placed onto RM5 medium to regenerate plants as in Example I. After 16 days, the callus was transferred to R5 medium as in Example I. After 25 d on R5 medium, plantlets were transferred to R5 medium and grown up for 20 days. At this point, plantlets were transferred to vermiculite for one week and then transplanted into soil where they are being grown to sexual maturity.

EXAMPLE III

The procedure of Example II was repeated exactly except that different plasmids were used.

The plasmids pBII221 and pHYGI1 described in Example I were used as well as pMS533 which is a plasmid that contains the insecticidal *Bacillus thuringiensis* endotoxin (BT) gene fused in frame with the neomycin phosphotransferase (NPTII) gene. At a position 5' from the fusion gene are located segments of DNA from the CaMV and nopaline synthase promoters. At a position 3' from the fusion gene are segments of DNA derived from the tomato protease inhibitor I gene and the poly A region of the nopaline synthase gene.

Callus was bombarded exactly as in Example I except that the DNA used in the tungsten/DNA preparations differed. Two tubes contained plasmids pHYGI1 and pMS533 and one tube contained plasmids pHYGI1 and pMS533 and one tube contained no plasmid but contained 5 µl TE-1 (10 mM Tris-HCl pH 8.0, 1 mM EDTA pH 8.0).

The following bombardments were done: 9×pHYGI1/pMS533 (potential positive treatment) and 2×TE prep (control treatment).

After bombardment, the callus from the pHYGI1/pMS533 treatments was placed onto round 1 selection plates, F medium containing 15 mg/l hygromycin, as ten 25 mg pieces per plate. The same was done for one of the plates bombarded with the TE preparation (selected control callus). One plate of callus bombarded with the TE preparation was placed onto F medium with no hygromycin; this callus was maintained throughout the ongoing experiment as a source of control tissue (unselected control callus).

After 12 days, the callus on round 1 selection plates appeared to show about 90% of the weight gain of the unselected control callus All of the callus was transferred from round 1 selection plates to round 2 selection plates containing 60 mg/l hygromycin as ten 30 mg pieces per plate. After 22 days of selection on round 2 selection plates, the callus appeared completely uninhibited. All of the callus was transferred from round 2 selection plates to round 3 selection plates containing 60 mg/l hygromycin.

At 74 days post-bombardment, a single viable sector was observed proliferating from the surrounding necrotic tissue. The callus line was from pHYGI1/pMS533 treated material and was designated 86R. The callus line 86R was transferred to F medium.

After 24 days, the callus line 86R had grown substantially. Portions of the callus were then transferred to (i) F media containing 15 mg/l hygromycin, and (ii) F media containing 60 mg/l hygromycin. Control callus was plated on F media with 15 mg/l hygromycin.

After 19 days of culture, the callus line 86R appeared to grow rapidly and was uninhibited on both levels of hygromycin. The control callus appeared to have only about 50% of the weight gain of 86R. The callus lines were transferred to fresh media at the same respective levels of hygromycin to further test the resistance of the callus line 86R. After 26 days of culture, the callus line 86R appeared uninhibited on 60 mg/l hygromycin.

Southern blots were performed on DNA isolated from the callus line 86R and control callus to confirm the presence of the hygromycin resistance gene and to determine whether the BT gene was present.

For detection of the HPT coding sequence, DNA isolated from 86R callus and control callus was digested with the restriction enzymes BamHI, XhoI, or PstI as described in Examples I and II. After hybridization with a probe prepared from the HPT coding sequence, the following bands were observed. For the BamHI digest, bands were observed at the expected size of 1.05 Kb as well as at approximately 3.0 and 2.3 Kb. This result demonstrates that the HPT coding sequence is present in the callus line 86R. The additional bands at 3.0 and 2.3 Kb indicate that either digestion was incomplete or that multiple rearranged copies are present. For the XhoI digest, a single band was observed at approximately 5.1 Kb. Because XhoI does not cut pHYGI1, this suggests incorporation of the hygromycin construct into DNA different than pHYGI1. For the PstI digestion, a large band was observed at approximately 5.1 Kb. This band appeared to be two fragments of similar molecular weight. Two or more bands would be expected from a PstI digestion if the gene was incorporated into high molecular weight DNA. In no case was hybridization observed for DNA from control callus for any of the above-mentioned digestions.

For detection of the BT gene, a Southern blot was carried out on DNA isolated from 86R and control callus digested with the enzymes BamHI and XhoI in combination. A BamHI, XhoI co-digestion liberates the 1.8 Kb BT coding sequence from the pMS533 construction used in this transformation. The blot prepared was hybridized to a probe prepared from the 1.8 Kb BT coding sequence. A band was observed for 86R DNA at the expected size of 1.8 Kb whereas no hybridization was observed for control DNA. Additional bands of much lesser intensity were also observed for 86R DNA. This result demonstrates that the BT coding sequence is present in the callus line 86R. This further demonstrates the introduction into maize of an unselected gene with potential commercial value. The name of callus line 86R was changed to CB1.

Plants are being regenerated from CB1 callus and control callus as described in Example I.

The invention has been described with reference to various specific and preferred embodiments and techniques. However, it should be understood that many variations and modifications may be made while remaining within the spirit and scope of the invention.

What is claimed is:

1. A fertile transgenic *Zea mays* plant containing an isolated heterologous DNA construct encoding EPSP synthase wherein said DNA construct is expressed so that the plant exhibits resistance to normally toxic levels of glyphosate, wherein said resistance is not present in a *Zea mays* plant not containing said DNA construct, and wherein said DNA construct is transmitted through a complete normal sexual cycle of the transgenic plant to the progeny generation.

2. The transgenic plant of claim 1 wherein the heterologous DNA construct comprises a promoter.

3. A seed produced by the transgenic plant of claim 1 which comprises said heterologous DNA construct.

4. A progeny transgenic *Zea mays* plant derived from the transgenic plant of claim 1 wherein said progeny plant expresses said heterologous DNA construct so that the progeny plant exhibits said glyphosate tolerance.

5. A seed derived from the progeny plant of claim 4 wherein said seed comprises said heterologous DNA construct.

6. The transgenic plant of claim 1 wherein the plant is obtainable by a process comprising the steps of:
   (i) bombarding intact regenerable *Zea mays* cells with microprojectiles coated with said heterologous DNA construct;
   (ii) identifying or selecting a population of transformed cells; and
   (iii) regenerating a fertile transgenic plant therefrom.

* * * * *